(12) United States Patent
Schibel et al.

(10) Patent No.: US 11,752,497 B2
(45) Date of Patent: Sep. 12, 2023

(54) NANOPORE/NANOWELL ELECTRODE ENABLED EXONUCLEASE SEQUENCING

(71) Applicant: ELECTRONIC BIOSCIENCES, INC., San Diego, CA (US)

(72) Inventors: Anna E. P Schibel, Snoqualmie, WA (US); Eric N. Ervin, Holladay, UT (US); Sean German, Salt Lake City, UT (US)

(73) Assignee: ELECTRONIC BIOSCIENCES, INC., San Diego, CA (US)

( * ) Notice: Subject to any disclaimer, the term of this patent is extended or adjusted under 35 U.S.C. 154(b) by 660 days.

(21) Appl. No.: 16/605,728

(22) PCT Filed: Apr. 18, 2018

(86) PCT No.: PCT/US2018/028200
§ 371 (c)(1),
(2) Date: Oct. 16, 2019

(87) PCT Pub. No.: WO2018/195222
PCT Pub. Date: Oct. 25, 2018

(65) Prior Publication Data
US 2020/0171487 A1 Jun. 4, 2020

Related U.S. Application Data

(60) Provisional application No. 62/487,414, filed on Apr. 19, 2017.

(51) Int. Cl.
*C12Q 1/6869* (2018.01)
*B01L 3/00* (2006.01)
*G01N 33/487* (2006.01)

(52) U.S. Cl.
CPC .......... *B01L 3/5027* (2013.01); *C12Q 1/6869* (2013.01); *G01N 33/48721* (2013.01);
(Continued)

(58) Field of Classification Search
CPC ............ C12Q 1/6869; C12Q 2521/319; C12Q 2521/543; B01L 2300/0636;
(Continued)

(56) References Cited

U.S. PATENT DOCUMENTS

2008/0041733 A1 2/2008 Hibbs et al.
2014/0106360 A1 4/2014 Hayden
(Continued)

FOREIGN PATENT DOCUMENTS

KR 10-2012-0126599 A 11/2012
WO WO-2007057668 A1 * 5/2007 ........... C12Q 1/6869
(Continued)

OTHER PUBLICATIONS

Sampath, G., "A tandem cell for nanopore-based DNA sequencing with exonuclease," RSC Advances, vol. 5, pp. 167-171. (Year: 2015).*
(Continued)

*Primary Examiner* — Young J Kim
(74) *Attorney, Agent, or Firm* — Greer, Burns & Crain, LTD.; Gregory P. Einhorn

(57) ABSTRACT

Devices and methods are provided for identifying individual monomeric units in sequential order as they are released or cleaved from a polymer strand via an enzyme, which acts on the polymer, and the monomeric units translocate through a transmembrane channel. Methods are also provided for identifying molecules as they translocate through a transmembrane channel.

23 Claims, 15 Drawing Sheets

(52) U.S. Cl.
CPC ............... *B01L 2300/0636* (2013.01); *B01L 2300/0858* (2013.01); *B01L 2400/0418* (2013.01); *B01L 2400/0421* (2013.01)

(58) Field of Classification Search
CPC ..... B01L 2300/0858; B01L 2400/0421; B01L 3/5027
See application file for complete search history.

(56) References Cited

U.S. PATENT DOCUMENTS

| | | |
|---|---|---|
| 2014/0262784 A1 | 9/2014 | Clarke et al. |
| 2014/0349300 A1 | 11/2014 | Meuleman |
| 2015/0159213 A1 | 6/2015 | Turner et al. |
| 2016/0115531 A1 | 4/2016 | Huber et al. |
| 2016/0327507 A1* | 11/2016 | Davis ............... G01N 27/3277 |
| 2017/0058336 A1 | 3/2017 | Ivankin et al. |
| 2019/0195884 A1* | 6/2019 | Lindsay ............. G01N 33/6821 |

FOREIGN PATENT DOCUMENTS

| | | |
|---|---|---|
| WO | 2016/065300 A1 | 4/2016 |
| WO | WO 2018/195222 A1 | 10/2018 |

OTHER PUBLICATIONS

Clarke et al., "Continuous base identification of single-molecule nanopore DNA sequencing," Nature Nanotechnology, April, vol. 4, pp. 265-270. (Year: 2009).*

Hermanova et al., "Graphene oxide immobilized enzymes show high thermal and solvent stability," Nanoscale, vol. 7, pp. 5852-5858. (Year: 2015).*

"International Preliminary Report on Patentability dated Oct. 31, 2019 in International Patent Application No. PCT/US2018/028200, filed on Apr. 18, 2018", 15 pages.

"International Search Report and Written Opinion dated Aug. 21, 2018 in International Patent Application No. PCT/US2018/028200, filed on Apr. 18, 2018", 22 pages.

"Invitation to Pay Additional Fees dated Jun. 27, 2018 in International Patent Application No. PCT/US2018/028200, filed on Apr. 18, 2018", 16 pages.

Clarke, et al., "Continuous Base Identification for Single-Molecule Nanopore DNA Sequencing", Nature Nanotechnology, Apr. 2009, 4(4):265-270.

Rusk, Nicole "Cheap Third-Generation Sequencing", Nature Methods, Apr. 2009, 6(4):244-245.

* cited by examiner

NANOPORE/NANOWELL ELECTRODE ENABLED EXONUCLEASE SEQUENCING

RELATED PATENT APPLICATION

This patent application is a 35 U.S.C. 371 national phase patent application of PCT/US2018/28200, filed on Apr. 18, 2018, entitled NANOPORE/NANOWELL ELECTRODE ENABLED EXONUCLEASE SEQUENCING, naming Anna E. P. Schibel, Eric N. Ervin and Sean German as inventors, which claims the benefit of U.S. Provisional Patent Application No. 62/487,414 filed on Apr. 19, 2017, entitled "NANOPORE/NANOWELL ELECTRODE ENABLED EXONUCLEASE SEQUENCING," naming Anna E. P. Schibel and Eric N. Ervin as inventors. The entire content of the foregoing patent applications are incorporated herein by reference, including all text, tables and drawings.

FIELD

The technology relates in part to nanopore devices and methods of use. Such devices are useful for sensing target molecules and sequencing biopolymers, for example.

BACKGROUND

Devices having relatively small diameter channels can be used to detect small molecules and can be used to sequence biopolymers (e.g., DNA, RNA, peptides, polypeptides). Certain devices have channels with diameters in the nanometer range, and sometimes are referred to as "nanopore" devices. Such devices often are constructed from a nonconductive material such as glass or quartz for example.

A device can have a membrane protein having a relatively small pore inserted in a lipid bilayer. An example of such a membrane protein is alpha-hemolysin.

SUMMARY

Provided herein, in certain aspects, is a device comprising a substrate comprising a chamber comprising a proximal opening, a distal opening, sidewalls and an interior volume. A first seal is over the proximal opening of the chamber and a second seal over the distal opening of the chamber; whereby the interior volume of the chamber is a confined volume. A transmembrane channel is in the first seal. An enzyme is attached to an interior surface of the chamber and a component configured to detect an interaction between a molecule and the transmembrane channel.

Also provided in certain aspects is a multiplex device comprising more than one of the described devices.

Also provided in certain aspects is a method for determining the sequence of a polymer, comprising: a) electrophoretically and/or electroosmotically driving a polymer from a bulk solution through a transmembrane channel into a confined volume of a chamber; whereby the polymer contacts an enzyme in the confined volume of the chamber, under conditions in which the enzyme cleaves monomeric units from the polymer; b) electrophoretically and/or electroosmotically driving monomeric units in the order which they are sequentially cleaved from the polymer by the enzyme out of the confined volume of the chamber through the transmembrane channel; and c) determining the identity of each of the monomeric units based on its current signature, translocation time, and/or associated current noise level modulation as the monomeric unit translocates through the transmembrane channel, thereby determining the sequence of the polymer.

Also provided in certain aspects is a method for determining the sequence of a polymer or a portion thereof, comprising: a) electrophoretically and/or electroosmotically driving a polymer from a bulk solution, through a transmembrane channel into a confined volume of a chamber; whereby the polymer contacts an enzyme in the confined volume of the chamber, under conditions in which the enzyme cleaves monomeric units from the polymer; b) electrophoretically and/or electroosmotically driving a first monomeric unit cleaved from the polymer out of the confined volume of the chamber through the transmembrane channel; c) upon detection of a translocation of the first monomeric unit through the transmembrane channel, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel into the confined volume of the chamber; d) upon detection of a translocation of the first monomeric unit through the transmembrane channel, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel out of the confined volume of the chamber; e) repeating steps c and d multiple times; f) determining the identity of the first monomeric unit based on its current signature, translocation time, and/or associated current noise level modulation as the monomeric unit translocates through the transmembrane channel multiple times; g) electrophoretically and/or electroosmotically driving a next monomeric unit sequentially cleaved from the polymer by the enzyme out of confined volume of the chamber through the transmembrane channel; h) upon detection of a translocation of the next monomeric unit through the transmembrane channel, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel into the confined volume of the chamber; i) upon the detection of a translocation of the next monomeric unit through the transmembrane channel, triggering a reversal of DC drive bias used to electrophoretically and/or electroosmotically drive the next monomeric units through the transmembrane channel, whereby the next monomeric unit is electrophoretically and/or electroosmotically driven back through the transmembrane channel out of the confined volume of the chamber; j) repeating steps h and i multiple times; k) determining the identity of the next monomeric unit based on its current signature, translocation time, and/or associated current noise level modulation as the next monomeric unit translocates through the transmembrane channel multiple times; and l) repeating steps g to k until the identity of all monomeric units of the polymer or a portion of the monomeric units of the polymer have been identified, thereby determining the sequence of the polymer or a portion thereof.

Also provided in certain aspects is a method for determining the sequence of a polymer or a portion thereof, comprising: a) electrophoretically and/or electroosmotically driving the polymer from the bulk solution, through the transmembrane channel into the confined volume of the chamber; whereby the polymer contacts an enzyme in the confined volume of the chamber, under conditions in which the enzyme cleaves monomeric units from the polymer; b) electrophoretically and/or electroosmotically driving a first monomeric unit cleaved from the polymer by the enzyme out of the confined volume of the chamber through the transmembrane channel; c) upon detection of a translocation of the first monomeric unit through the transmembrane channel triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel into the confined volume of the chamber; d) after a period of about 5 microseconds to about 500 microseconds, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel out of the confined volume of the chamber; e) after a period of about 5 microseconds to about 500 microseconds triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel into the confined volume of the chamber; f) after a period of about 5 microseconds to about 500 microseconds, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel out of the confined volume of the chamber; g) repeating steps e and f multiple times; h) determining the identity of the first monomeric unit based on its current signature, translocation time, and/or associated current noise level modulation as the monomeric unit translocates through the transmembrane channel multiple times; i) electrophoretically and/or electroosmotically driving a next monomeric unit sequentially cleaved from the polymer by the enzyme out of the confined volume of the chamber through the transmembrane channel; j) upon detection of a translocation of the next monomeric unit through the transmembrane channel, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel into the confined volume of the chamber; k) after a period of about 5 microseconds to about 500 microseconds, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel out the confined volume of the chamber; l) after a period of about 5 microseconds to about 500 microseconds, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel into the confined volume of the chamber; m) after a period of about 5 microseconds to about 500 microseconds, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel out the confined volume of the chamber; n) repeating steps l and m multiple times; o) determining the identity of the next monomeric unit based on its current signature, translocation time, and/or associated current noise level modulation as the next monomeric unit translocates through the transmembrane channel multiple times; and p) repeating steps i to o until the identity of all monomeric units of the polymer or a portion of the monomeric units of the polymer have been identified, thereby determining the sequence of the polymer or a portion thereof.

Also provided in certain aspects is a method for determining the identity of a molecule, comprising: a) electrophoretically and/or electroosmotically driving a molecule through a a transmembrane channel; b) upon the detection of a translocation of the molecule, triggering a reversal of the DC drive bias used to electrophoretically and/or electroosmotically drive the molecule through the transmembrane channel, whereby the molecule is driven back through the transmembrane channel; c) upon the detection of a translocation event, triggering a reversal of DC drive bias used to drive the molecule through the transmembrane channel, whereby the molecule is electrophoretically and/or electroosmotically driven back through the transmembrane channel; d) repeating b and c multiple times; and e) determining the identity of the molecule based on its current signature, translocation time, and/or associated current noise level modulation as it translocates through the transmembrane channel multiple times.

Also provided in certain aspects is a method for determining the identity of a molecule, comprising: a) electrophoretically and/or electroosmotically driving a molecule through a transmembrane channel; b) upon the detection of a molecule translocation event, triggering a reversal of DC drive bias used to drive the molecule through the transmembrane channel, whereby the molecule is electrophoretically and/or electroosmotically driven back through the transmembrane channel; c) after a period of about 5 microseconds to about 500 microseconds, triggering a reversal of DC drive bias, whereby the molecule is electrophoretically and/or electroosmotically driven back through the transmembrane channel; d) after a period of about 5 microseconds to about 500 microseconds triggering a reversal of DC drive bias, whereby the molecule is electrophoretically and/or electroosmotically driven back through the transmembrane channel; e) repeating c and d multiple times; and f) determining the identity of the molecule based on its current signature, translocation time, and/or associated current noise level modulation as it translocates through the transmembrane channel multiple times.

Also provided in certain aspects is device, comprising a substrate comprising a chamber that comprises a proximal opening, a distal opening, an interior volume and an electrode enclosing the distal opening of the chamber. An enzyme having exonuclease activity attached to the electrode, wherein the enzyme optionally is attached by a covalent attachment to the electrode. A planar lipid bilayer suspended over the proximal opening of the chamber and enclosing the interior volume. A transmembrane channel in the planar lipid bilayer; and a component configured to detect an interaction between a molecule and the transmembrane channel.

Also provided in certain aspects is a method for determining the sequence of a polymer, comprising: (A) providing a device as described with a bulk solution outside the chamber comprising a polymer; (B) electrophoretically driving the polymer from the bulk solution, through the transmembrane channel into the interior volume of the chamber under conditions in which the enzyme can cleave monomers from the polymer; (C) electrophoretically driving the monomers out of the enclosed chamber volume through the transmembrane channel in sequential order; (D) determining the identity of the monomers based on its current signature as it translocates through the transmembrane channel; and (E) repeating C and D until the sequence of the polymer is determined.

Also provided in certain aspects is a method for determining the sequencing of a polymer, comprising: (A) providing a device as described with a bulk solution outside the chamber comprising a polymer; (B) electrophoretically driving the polymer from the bulk solution, through the transmembrane channel into the interior volume of the chamber under conditions in which the enzyme can cleave monomers from the polymer; (C) electrophoretically driving the monomers out of the enclosed chamber volume through the transmembrane channel in sequential order; (D) upon the detection of the monomer translocation event, triggering a reversal of the DC drive bias used to electrophoretically drive the monomer through the transmembrane channel, such that the monomer is electrophoretically driven back through the transmembrane channel back into the chamber; (E) upon the detection of the translocation event, triggering a reversal of the DC drive bias used to electrophoretically drive the monomer through the transmembrane channel, such that the monomer is electrophoretically driven back through the transmembrane channel back out of the chamber; (F) repeating D and E a set number of times; (G) determining the identity of the monomers based on its current signature as it translocates through the transmembrane channel multiple times; and (H) repeating D, E, F and G until the sequence of the polymer is determined.

Also provided in certain aspects is a method for determining the sequencing of a polymer, comprising: (A) providing a device as described with a bulk solution outside the chamber comprising a polymer; (B) electrophoretically driving the polymer from the bulk solution, through the transmembrane channel into the interior volume of the chamber under conditions in which the enzyme can cleave monomers from the polymer; (C) electrophoretically driving the monomers out of the enclosed chamber volume through the transmembrane channel in sequential order; (D) upon the detection of the monomer translocation event, triggering a reversal of the DC drive bias used to electrophoretically drive the monomer through the transmembrane channel, such that the monomer is electrophoretically driven back through the transmembrane channel back into the chamber; (E) after a set amount of time, triggering a reversal of the DC drive bias such that the monomer is electrophoretically driven back through the transmembrane channel back out of the chamber; (F) after a set amount of time, triggering a reversal of the DC drive bias such that the monomer is electrophoretically driven back through the transmembrane channel back into the chamber; (G) repeating E and F a set number of times; (I) determining the identity of the monomers based on its current signature as it translocates through the transmembrane channel multiple times; and (J) repeating E, F, G and I until the sequence of the polymer is determined.

Also provided in certain aspects is a method for determining the identity of a molecule, comprising: (A) electrophoretically driving the molecule through a transmembrane channel; (B) upon the detection of the molecule translocation event, triggering a reversal of the DC drive bias used to electrophoretically drive the molecule through the transmembrane channel, such that the molecule is electrophoretically driven back through the transmembrane channel; (C) upon the detection of the translocation event, triggering a reversal of the DC drive bias used to electrophoretically drive the molecule through the transmembrane channel, such that the molecule is electrophoretically driven back through the transmembrane channel; (D) repeating B and C a set number of times; and (E) determining the identity of the molecule based on its current signature as it translocates through the transmembrane channel multiple times.

Also provided in certain aspects is a method for determining the identity of a molecule, comprising: (A) electrophoretically driving the molecule out through a transmembrane channel; (B) upon the detection of the molecule translocation event, triggering a reversal of the DC drive bias used to electrophoretically drive the molecule through the transmembrane channel, such that the molecule is electrophoretically driven back through the transmembrane channel; (C) after a set amount of time, triggering a reversal of the DC drive bias such that the molecule is electrophoretically driven back through the transmembrane channel; (D) after a set amount of time, triggering a reversal of the DC drive bias such that the molecule is electrophoretically driven back through the transmembrane channel; (E) repeating C and D a set number of times; and (F) determining the identity of the molecule based on its current signature as it translocates through the transmembrane channel multiple times;

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 1A depicts the associated platform (not drawn to scale). FIG. 1B depicts the theoretical current as a function of time trace workflow.

FIG. 2A depicts the associated platform (not drawn to scale). FIG. 2B depicts the theoretical current as a function of time trace workflow.

FIG. 3A represents current as a function of time traces for AMP vs. M$^6$AMP. FIG. 3B represents the associated translocation current blocking level histograms (100 kHz black curve (left), 10 kHz red curve (right)).

FIG. 4 is a schematic of the finite element model used for testing the feasibility of nucleotide-by-nucleotide sequencing using an exonuclease in a confined volume (not to scale).

DETAILED DESCRIPTION

Figure 1A:
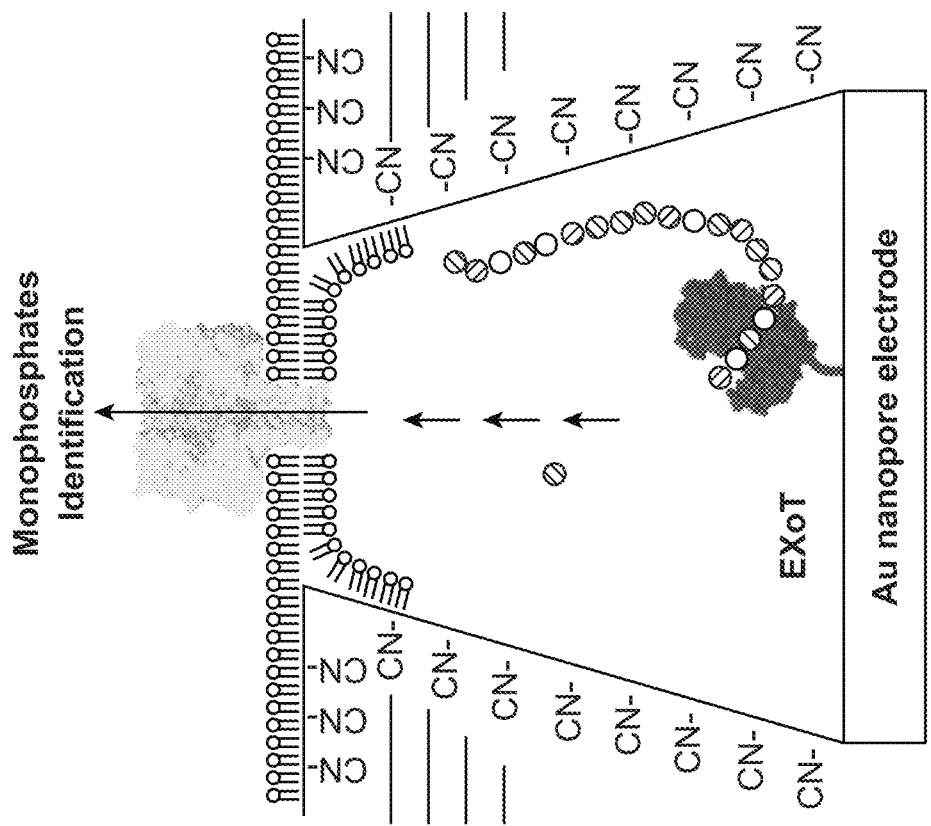
FIGS. 1A and 1B represent a conceptualization of the Nanopore/Nanowell Electrode Enabled Exonuclease Sequencing method for RNA.

While there has been very significant progress made towards improving the accuracy, increasing the read lengths, reducing the associated time and cost, and increasing the accessibility of nucleic acid sequencing technologies over the last five or so years, most of the major and enabling advancements made do not exploit the full potential utility of sequencing due to the fact that they cannot identify all known and unknown nucleic acid modifications. As an example, the standard method for sequencing RNA (RNA-seq) proceeds via reverse transcription and cDNA next generation sequencing. The main issues with this process are that it requires very high-quality RNA, the reverse transcription introduces biases/artifacts which may interfere with characterization, and it results in the loss of the nucleotide modification identities present in the original strands. A methodology/technology capable of directly sequencing RNA, without transcription, with extremely high accuracy and the inherent ability to identify all known and unknown RNA modifications has the potential to revolutionize the use of the transcriptome and epitranscriptome; radically changing standard practices as well as creating and enabling entirely new fields (e.g. epitranscriptomic diagnostics and therapeutics).

At present, the scientific communities understanding of the "epitranscriptome," i.e. the chemical modifications which regulate the function of RNA, is still in its infancy.[1] While there are over 100 known RNA nucleotide modifications, due to the lack of analytical characterization methods available, the exact role of these modifications remains to be determined. In the majority of hard to characterize RNA modification cases, the presence of the modification does not affect the Watson-Crick base pairing ability of the modified base relative to its unmodified counterpart. Thus, it is still able to pair with a complementary base, and can be reverse transcribed, making it undetectable by traditional hybridization and sequencing-based methods. Typically, detection requires thin-layer chromatography or mass spectrometry on purified and fragmented RNA for detection, an approach that is labor-intensive, low-throughput, and prohibitive to genome-wide characterization, i.e. the entire genome, including >360,000 mRNA molecules per cell (~2 kb/mRNA). Alternatively, $N^6$-methyladenosine ($m^6A$), a RNA modification that is the most prevalent internal (non-cap) RNA modification known to exist in higher eukaryotes, having previously been observed in viruses, yeast, plants, mice, and humans, is now believed to account for 0.1-0.4% of adenosines or 3-5 $m^6A$ per mRNA molecule, and has been shown to be associated cancer initiation and progression. Toward its characterization, $m^6A$ has been investigated by incubating cells with $^{14}C$-radiolabled methionine (the precursor for endogenous methyl donor, S-adenosylmethionine), allowing the incorporation of methyl groups into RNA to be quantified. Unfortunately, this method does not provide information about the sequence context for the modification nor can it be used to identify the specific RNAs that contain $m^6A$. Recently, two groups have independently demonstrated the ability to assess $m^6A$ by combining methylated RNA immunoprecipitation with next generation sequencing (MeRIP-Seq and $m^6A$-seq). In this strategy, RNA fragments containing $m^6A$ are isolated from bulk solution via antibodies that specifically recognize $m^6A$, after which, these $m^6A$-enriched fragments are sequenced and then aligned with larger reference genomes to identify sequence contexts. While these methods have provided information on conserved $m^6A$ motifs, they remain qualitative in nature, i.e. the abundance of $m^6A$ per RNA fragment is not easily determined. All of these studies in combination highlight the lack of quantitative experimental tools available for characterizing and sequencing RNA modifications, and there are similar difficulties in characterizing and sequencing DNA modifications.

Novel nanopore-based approaches however, are potentially ideally suited for nucleic acid modification characterization because of their ability to discriminate between slight variations in molecular size and chemical make-up, along with their potential for high throughput. Since Church et al. first proposed the idea of polymer sequencing using a nanopore in 1995, nanopores have been extensively studied for their ability to directly sequence nucleic acids. Although these studies have proved to be tremendously valuable, with nanopore-based sequencing quickly becoming a reality, the advancements made (e.g. motor protein or enzyme assisted processivity/translocation) do not necessarily lend themselves to extremely high (<99%) accuracy or the ability to correctly identify modifications, nor do they transfer over to direct RNA sequencing. That being said, recent studies have shown that nanopores can also be useful tools for studying RNA. Indeed, numerous groups, using both biological and solid state nanopores, have demonstrated the ability to translocate RNA of varying lengths to and through nanopores, and have further been able to quantify the concentration of specific RNA targets based on their associated capture rate. The methodology introduced here, termed Nanopore/Nanowell Electrode Enabled Exonuclease Sequencing, is capable of nucleic acid sequencing, including direct RNA sequencing without a cDNA intermediate, with the inherent ability to identify nucleic acid modifications.

Nanopore/Nanowell Electrode Devices

Figure 11:
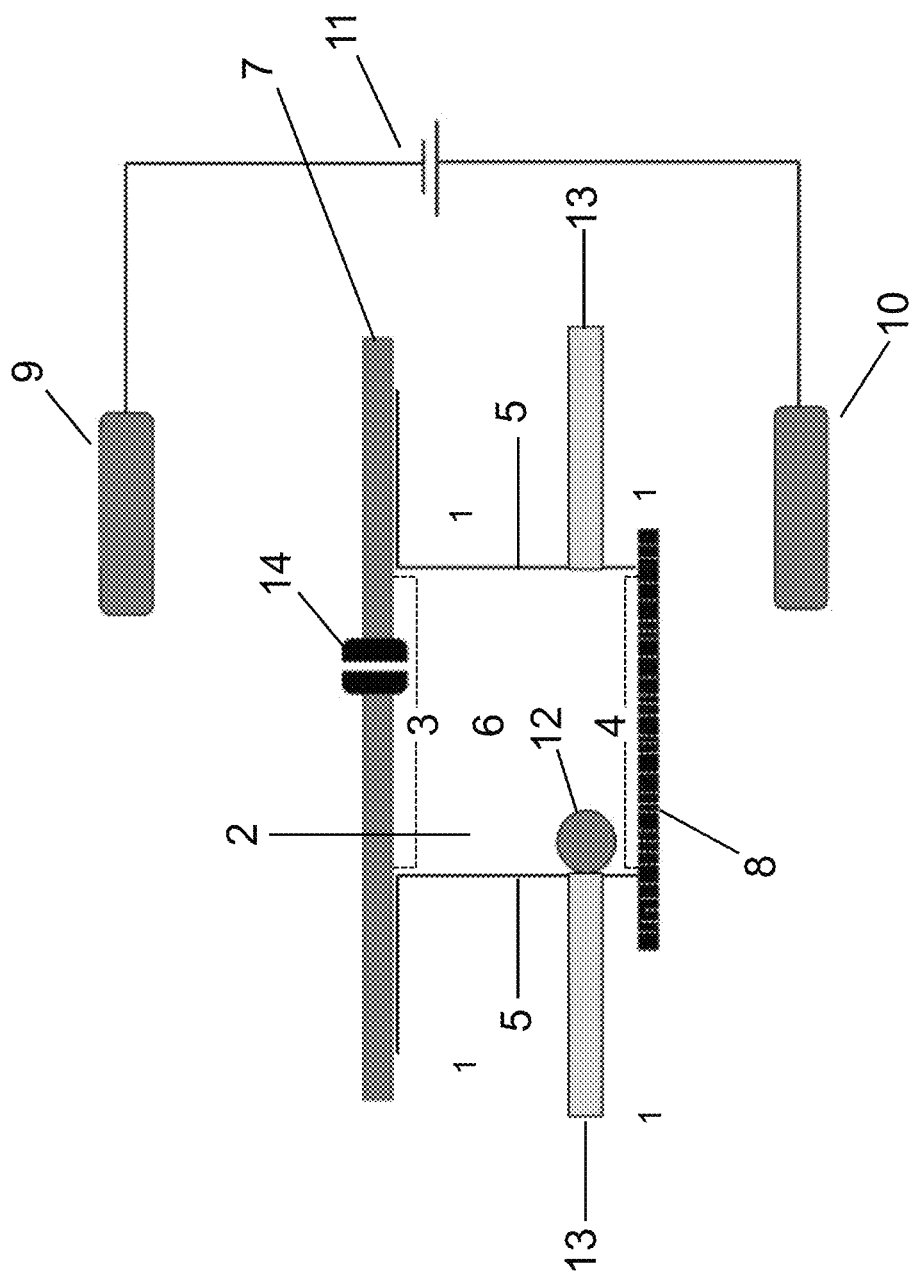
FIG. 11 shows an alternative embodiment of a nanopore/nanowell electrode having a first electrode external to a chamber and opposed to but not covering a proximal opening of a chamber, a second electrode external to a chamber, opposed to and not covering a distal opening of a chamber and not in contact with a second seal and an enzyme attached to a side of a chamber.

A non-limiting embodiment of a nanopore/nanowell electrode device is shown in FIG. 11. A nanopore/nanowell electrode device can include a substrate, a chamber comprising a proximal opening, a distal opening, sidewalls and an interior volume. A first seal is over a proximal opening of a chamber and a second seal is over a distal opening of a chamber, whereby the interior volume of the chamber is a confined volume, A transmembrane channel is in a first seal; an enzyme is attached to an interior surface of a chamber. A component is configured to detect an interaction between a molecule and a transmembrane channel.

In some embodiments, a nanopore/nanowell electrode device comprises a substrate as a solid support and/or an insulator (e.g., 1 in FIG. 11). In some embodiments, a substrate of a device can be manufactured from any suitable material. Non-limiting examples of materials suitable for use in a substrate of a device include, but are not limited to, Si, SiN, $Si_3N_4$, $SiO_2$, glass, quartz, aluminum, kapton, paralene, polyimide, diamond, fused silica or combinations thereof.

In some embodiments, a substrate comprises a chamber (e.g., 2 in FIG. 11).

In certain embodiments, a chamber comprises a proximal opening (e.g., 3 in FIG. 11) a distal opening (e.g., 4 in FIG. 11), sidewalls (e.g., 5 in FIG. 11) and an interior volume (e.g., 6 in FIG. 11). A chamber can be any shape including, but not limited to, conical, cylindrical, cubical, trapezoidal, triangular, pyramidal or cuboidal.

In certain embodiments, a width of a proximal opening of a chamber is about 20 nanometers to about 5 micrometers, about 50 nanometers to about 3 micrometers, about 75 nanometers to about 1 micrometer, about 100 nanometers to about 1 micrometer or about 100, 200, 300, 400, 500, 600, 700, 800, 900 or 1000 nanometers.

In certain embodiments, a depth of a chamber from a proximal opening to a distal opening is about 20 nanometers to about 10 micrometers, about 50 nanometers to about 5 micrometers, about 75 nanometers to about 1 micrometer, about 100 nanometers to about 1 micrometer, or about 100, 200, 300, 400, 500, 600, 700, 800, 900 or 1000 nanometers.

In certain embodiments, a nanopore/nanowell electrode device has a first seal (e.g., 7 in FIG. 11) over a proximal opening of a chamber and a second seal (e.g., 8 in FIG. 11) over a distal opening of a chamber. A first and a second seal can enclose the chamber. An enclosed chamber can have an interior volume (6) that is a confined volume.

In some embodiments, a confined volume of a chamber is about 1 zeptoliter to about 1 nanoliter, about 100 zeptoliters to about 1 picoliter, about 1 attoliter to about 1 femtoliter, or about 0.1 attoliters, 1 attoliter, 10 attoliters, 30 attoliters, 125 attoliters, 500 attoliters or 1 femtoliter. In some embodiments, a chamber having a confined interior volume is nanowell. In some embodiments, a confined volume of a chamber contains an aqueous solution of a buffered electrolyte or an ionic solution.

In certain embodiments, a first seal is a planar lipid bilayer or triblock copolymer. In some embodiments, a first seal is a first membrane. Examples of materials suitable for use as a first membrane include, but are not limited to, Si, SiN, $Si_3N_4$, $SiO_2$, glass, quartz, aluminum, kapton, paralene, polyimide, diamond, or fused silica or combinations thereof.

In some embodiments, a second seal is a porous material or a second membrane. In certain embodiments, porous material and a second membrane can conduct ions in solution, but do not transport molecules, including, but not limited to, a polymer, a nucleic acid, single stranded RNA, single stranded DNA, a monomeric unit of a polymer, a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide. Examples of materials suitable for use as porous material include, but are not limited to, graphene, graphene oxide, boron nitride, carbon nanotubes, molybdenum disulfide, chemically modified glass frit, sol-gel, chemically modified sol-gel, or chemically modified anodic aluminum oxide. Examples of membranes suitable for use as a second membrane include, but are not limited to, a proton exchange polymer membrane, an anion exchange polymer membrane, a conductive ion exchange polymer membrane, an ion exchange redox polymer, a redox doped conducting polymer or an oil and water ion transfer membrane. Sometimes a second seal can have nanopores, ion channels, porins or transmembrane nanopores in a lipid bilayer or triblock copolymer. In certain embodiments, nanopores, ion channels, porins or transmembrane nanopores in a lipid bilayer or triblock copolymer of a second seal do not have to be the same as a transmembrane channel in a first seal and do not function as a sensor of a molecule as does a transmembrane channel in a first seal. In some embodiments a second seal (e.g., a porous material or second membrane) is not in contact with a second electrode (see FIG. 11). In some embodiments a second seal contacts a second electrode (see FIG. 12). In some embodiments, a second seal can be a coating of a second electrode or an extension of a second electrode (see FIG. 12).

In certain embodiments, a nanopore/nanowell has a second electrode covering a distal opening of a chamber and a second seal comprises the second electrode (see FIGS. 1A, 2A, 9 and 10).

Sometimes a second electrode is a second seal. In some embodiments, a chamber is above a second electrode that is a second seal.

Transmembrane Channels

In certain embodiments, a device has a transmembrane channel (e.g., 14 in FIGS. 11, 12 and 13 and FIGS. 1A and 2A) inserted into a first seal. A transmembrane channel can function as a sensor for a molecule, as a device has a component to detect an interaction between a molecule and a transmembrane channel. In certain embodiments, a device has a single transmembrane channel inserted in a first seal that functions as a sensor.

In certain embodiments, a first seal is a planar lipid bilayer, a triblock copolymer or a first membrane. In some embodiments, a transmembrane channel is a nanopore, an ion channel or a transmembrane protein. In some embodiments, a transmembrane channel is a biological nanopore, an ion channel or a transmembrane protein and a first seal is a planar lipid bilayer or a triblock copolymer. In some embodiments, a transmembrane channel is a nanopore, the nanopore is a solid state nanopore and first seal is a first membrane. A first membrane can be made of, but is not limited to, Si, SiN, $Si_3N_4$, $SiO_2$, glass, quartz, aluminum, kapton, paralene, polyimide, diamond, or fused silica or combinations thereof.

In certain embodiments, a transmembrane channel is alpha-hemolysin (αHL), aerolysin, *Mycobacterium smegmatis* porin A (MspA), *Escherichia coli* CsgG, or outer membrane protein F (OmpF).

In certain embodiments, a transmembrane channel is a mutated, engineered, chemically modified, or is a mutant form. In some embodiments, a transmembrane channel is modified via site directed mutagenesis or chemical modification.

In some embodiments, a transmembrane channel is modified with an adaptor molecule. An adaptor molecule can be, but is not limited to, a large bulky molecule or a cyclic molecule, attached to the interior of a transmembrane channel (e.g., a cyclodextrin). An adaptor molecule can narrow the diameter of a transmembrane channel and/or alter the chemistry of a channel so as to effect the interaction between a molecule and a channel. In certain embodiments, adaptors useful in the described devices and methods do not preclude a transmembrane channel modified with one or more adaptor molecules from translocating a polymer.

In some embodiments, a transmembrane channel includes a modification at the entrance of a transmembrane channel on the cis side and/or a modification at the exit of a transmembrane channel on the trans side. In some embodiments, a modification of a channel lowers the energy barrier of entry into a channel of a polymer translocating into a confined volume of the chamber and/or lowers the energy barrier of entry into a channel of a monomeric unit of a polymer translocating out of a confined volume of a chamber. In some embodiments, a modification of a transmembrane channel increases the contrast between monomeric units as they translocate through a channel. In some embodiments, a modification is a reduction of negative charge within a channel, an increase in positive charge within a channel, a reduction in overall channel charge, a reduction in cross sectional width of a channel, an elongation of a sensing zone of a channel, the incorporation of electrostatic or van der Waal traps within a channel or a sensing zone, an increase in the nonpolar groups within a channel or combinations thereof.

Modifications as described below are applicable to a transmembrane channel discussed herein in addition to other useful modifications.

Detection of the Interaction Between a Molecule and a Transmembrane Channel

In certain embodiments, a nanopore/nanowell electrode device comprises a component configured to detect an interaction between a molecule and a transmembrane channel comprises a first electrode external to a chamber and opposed to but not covering a proximal opening of a chamber (e.g., 9 in FIG. 11). A second electrode external to a chamber, opposed to and not covering a distal opening of the chamber and not in contact with the second seal (e.g., 10 in FIG. 11), a second electrode external to a chamber, opposed to and not covering a distal opening of a chamber and in contact with a second seal (e.g., 10 in FIGS. 12 and 13) or a second electrode covering a distal opening of a chamber and a second seal comprises a second electrode (e.g., see FIG. 10). In some embodiments, placement of a first and a second electrode in a space external to a chamber of a device is not restricted, as long as a first electrode is opposed to a proximal opening and a second electrode is opposed to a distal opening.

In certain embodiments, a first and a second electrode can be comprised of, but not limited to, Au, Ag, Ag/AgCl, Pt, or combinations thereof.

Figure 12:
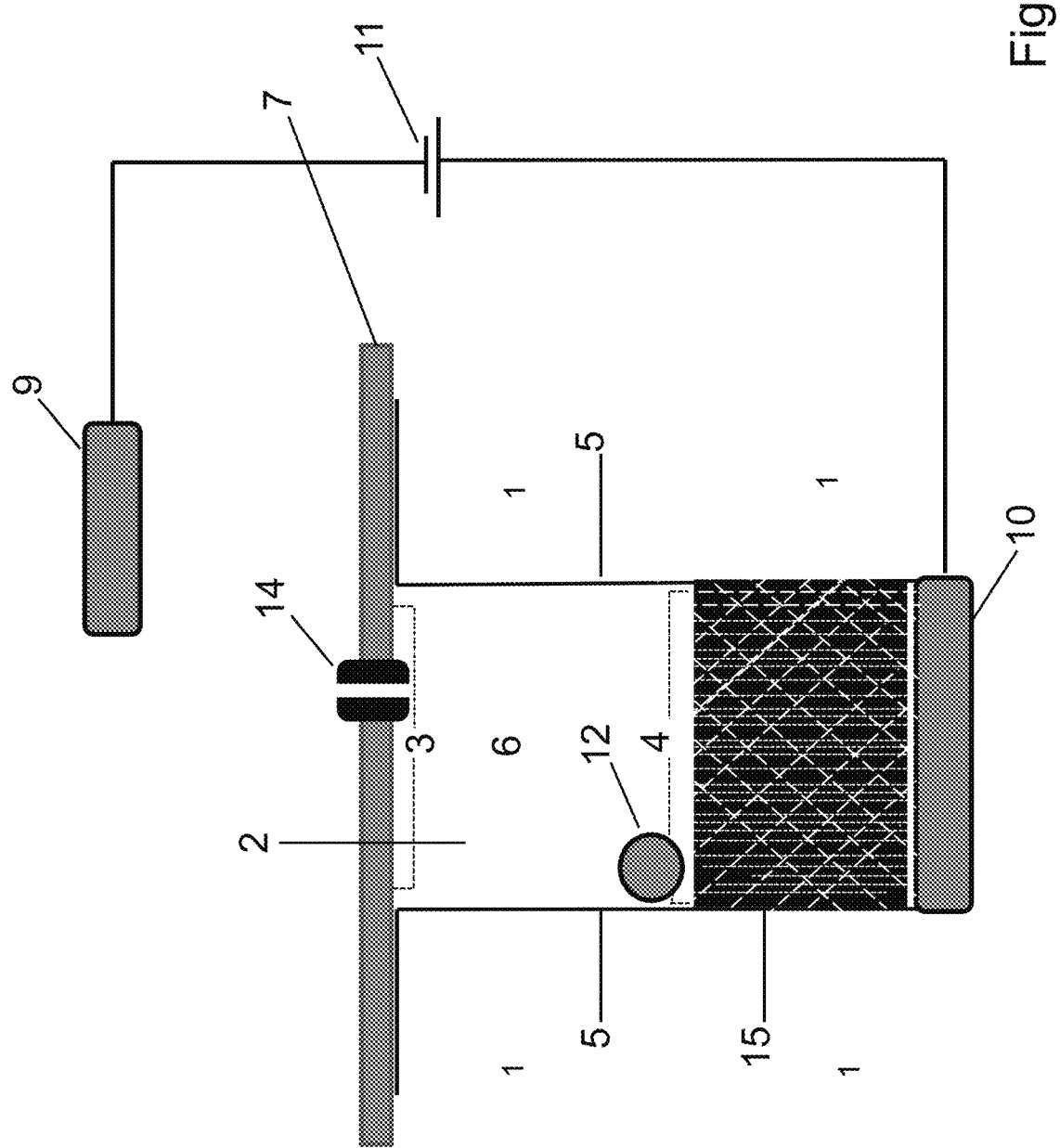
FIG. 12 shows an alternative embodiment of a nanopore/nanowell electrode having a first electrode external to a chamber and opposed to but not covering a proximal opening of a chamber, a second electrode external to a chamber, opposed to and not covering a distal opening of the chamber and in contact with a second seal and an enzyme attached to a second seal.
Figure 13:
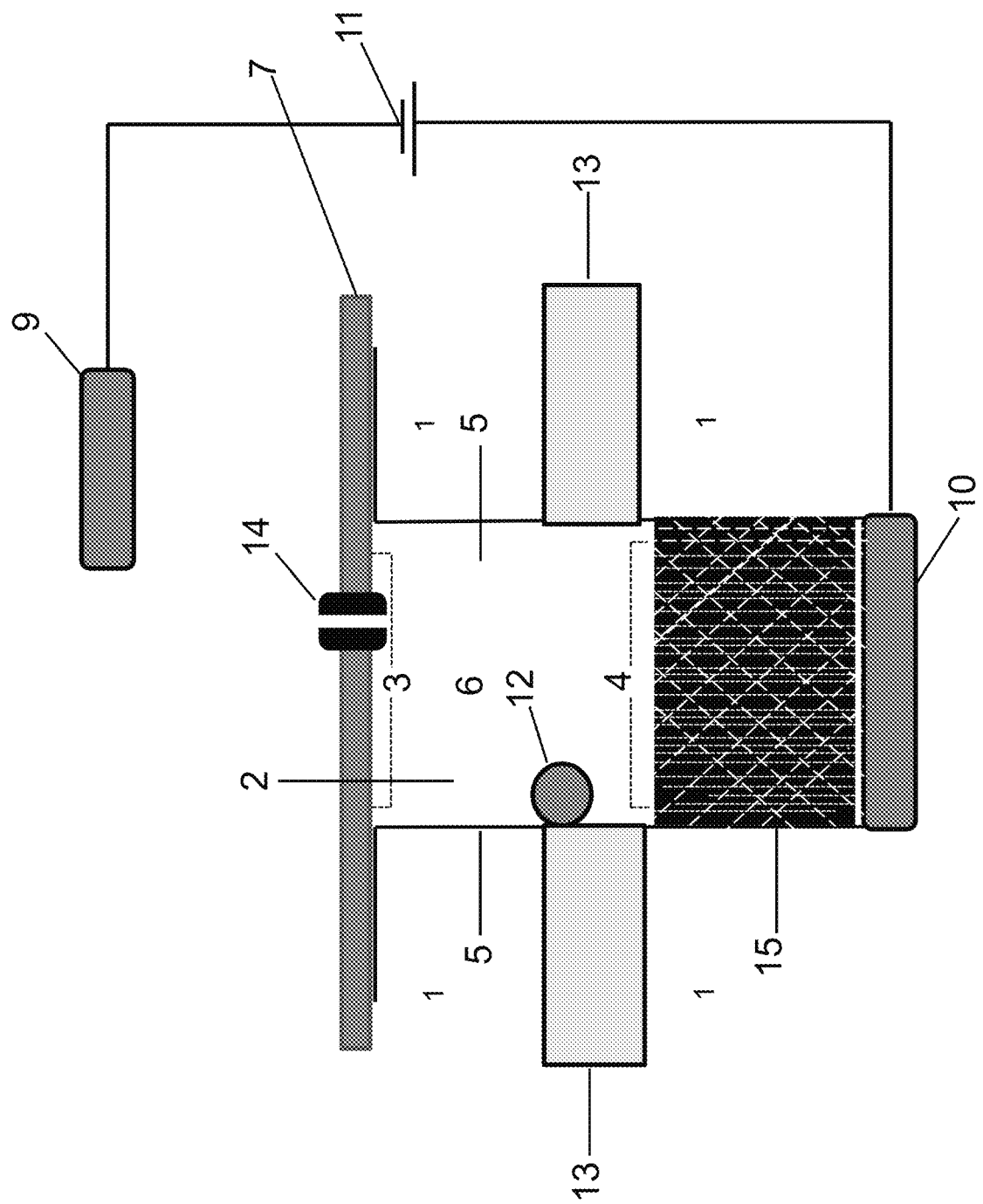
FIG. 13 shows an alternative embodiment of a nanopore/nanowell electrode having a first electrode external to a chamber and opposed to but not covering a proximal opening of a chamber, a second electrode external to a chamber, opposed to and not covering a distal opening of the chamber and in contact with a second seal and an enzyme attached to a side of a chamber.

In certain embodiments, a nanopore/nanowell electrode device has a component, in connection with a first and second electrode, configured to detect an interaction between a molecule and a transmembrane channel comprising a controllable voltage source associated with a capacity for DC and/or AC current measurements (e.g., 11 in FIGS. 11, 12 and 13). In some embodiments, a component can both control translocation of a molecule through a transmembrane channel of a device and also detect an interaction between a molecule and a transmembrane channel. In some embodiments, a component can control translocation of a charged molecule through a transmembrane channel electrophoretically by changing the strength and/or directionality of an electric field in which a device and/or transmembrane channel reside. In some embodiments, a component can control translocation of a molecule through a transmembrane channel electroosmotically by altering or modulating charge movement in the interior of a transmembrane channel. In some embodiments, translocation of a molecule through a transmembrane channel is controlled by electrophoresis and electroosmosis. In some embodiments, a component is configured to resolve and trigger high speed DC bias reversal. Often, high speed DC biasing capabilities are PPGA controlled.

In certain embodiments, a nanopore/nanowell electrode device detects an interaction between a molecule and a transmembrane channel by measuring a change in conductance of a channel (e.g. see FIG. 1A, current as a function of time plot). In certain embodiments, a nanopore/nanowell electrode device detects an interaction between a molecule and a transmembrane channel by detecting a current signature (e.g. see FIG. 1B, current as a function of time plot), translocation time (e.g., a period of time from the time of initiating electrophoretically and/or electroosmotically driving a molecule through a transmembrane channel to the time of detection of a translocation (conductance spike) and/or an associated current noise level modulation. A conductance spike detected as a result of a molecule interacting with a transmembrane channel as the molecule translocates through a channel typically exhibits a current noise level at the top of a peak. The current noise level at the top of a peak can be different for different molecules. Detection of modulation of this associated current noise level can be used to distinguish molecules that may exhibit peaks of similar amplitude and shape.

In some embodiments a component configured to detect an interaction between a molecule and a transmembrane channel comprises detectors (e.g., detector assemblies), microprocessors, computers or microprocessor controlled apparatuses, software, (e.g., a non-transitory computer-readable storage medium with an executable program stored thereon, wherein the program instructs a microprocessor to perform a function), a system (e.g., a system comprising one or more microprocessors and memory), the like or a combination thereof.

Molecules

A typical molecule that can be examined with a device described herein is a monomeric unit of a polymer and/or a polymer. In certain embodiments, a polymer is single stranded RNA or single stranded DNA molecule. In some embodiments, a transmembrane channel of a device can translocate a polymer into a confined volume of a chamber. Translocation of a polymer into a confined volume of a chamber is necessary for a polymer to contact an enzyme residing in a confined volume of a chamber. In some embodiments, a transmembrane channel of a device can translocate a full length single stranded RNA or single stranded DNA molecule into a confined volume of a chamber. In some embodiments, translocation of a full length single stranded RNA or single stranded DNA molecule allows for modified nucleotides to be identified and included in the sequence determined for an RNA or DNA strand. In some embodiments, translocation of a polymer can be facilitated by a device by modulating electrophoresis and/or electroosmosis, as described below.

In certain embodiments, a molecule is a monomeric unit of a polymer. In some embodiments, the monomeric unit is a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide.

Enzymes

In some embodiments, an enzyme can cleave one or more monomeric units from a polymer. In some embodiments, an enzyme can sequentially cleave one or more monomeric units or groups of monomeric units from a polymer. In some embodiments, an enzyme can cleave a nucleic acid polynucleotide. In some embodiments an enzyme has exonuclease activity. An exonucleases cleaves nucleotides from an end of a polynucleotide. In some embodiments an enzyme has endonuclease activity. An endonucleases cleaves a polynucleotide internally, within a strand or strands of a polynucleotide. Enzymes that cleave polymers, including exonuclease and endonucleases, are known to those who practice the art and could be identified as useful in a nanopore/nanowell electrode device described herein. Enzymes are also discussed below.

In certain embodiments, a nanopore/nanowell electrode device has an enzyme attached to an interior surface of a chamber (see FIGS. 1A, 1B and 9 and 12 in FIGS. 11 12 and 13). In some embodiments, there is a single enzyme molecule attached to an interior surface of a chamber. In some embodiments, there are two or more enzyme molecules attached to an interior surface of a chamber. In some embodiments, there are 1, 2, 3, 4, 5, 6, 7, 8, 9, 10, 11, 12, 13, 14, or 15 enzyme molecules attached to an interior surface of a chamber.

In certain embodiments, an enzyme is covalently attached, attached via a linker or attached via binding pairs to the inner surface of the chamber (e.g., as described below for an exonuclease). In some embodiments, an enzyme is attached to a side wall of a chamber. Sometimes an enzyme (12) can be attached to a metallic layer within/along a sidewall of a chamber (e.g., 13 in FIGS. 11 and 13) (multilayered substrate). In some embodiments, an enzyme is attached to a second electrode covering a distal opening of a chamber (see FIGS. 1A, 2A and 9). In some embodiments, an enzyme (12) is attached to a second seal covering a distal opening of a chamber that does not comprise a second electrode as part of the seal (e.g., 15 in FIG. 12).

In certain embodiments, an enzyme is attached to an inner surface of a chamber (as described above) at a distance from a first seal of about 10 nanometers to about 10 micrometers, about 10 nanometers to about 1 micrometer, about 10 nanometers to about 500 nanometers, about 50 nanometers to about 500 nanometers, about 100 nanometers to about 500 nanometer, or about 100, 125, 150, 175, 200, 225, 250, 275, 300, 325, 350, 375, 400, 425, 450, 475, 500, 600, 700, 800, 900, or 1000 nanometers. The position of an enzyme attached to an inner surface of a chamber (measured as a distance from a first seal) must provide sufficient clearance between the enzyme and the transmembrane channel to enable sequencing of a polymer.

ssDNA Exonucleases

DNA exonucleases are group of enzymatic proteins (nucleases) that break down poly-nucleic acids (DNA) by hydrolyzing the phosphodiester bonds of the strand to release a single deoxynucleotide monophosphate (dNMP) from the terminus. This differs from endonucleases which hydrolyze linkages within the strand. Nucleases are important for cellular metabolism, including nucleic acid repair, genetic recombination, and mutation avoidance as they remove potentially problematic (mismatched, modified, nicked, etc.) nucleotides. Nucleases are typically characterized by the following general criteria, but can possess overlapping characteristics. Nucleases can be classified by their substrate (DNA, RNA); their type of attack (endo or exo); their direction of attack, digesting DNA from the 3' or 5' direction based on functional group recognition (e.g. the presence of a 3'—OH group); and their preference for either single- or double-stranded (ss or ds, respectively) polynucleic acids. Furthermore, regardless of the direction of attack, nucleases can also be characterized by their hydrolysis product (e.g. mono- or oligo-nucleotides with either a 3'- or 5'-phosphate); a 3'- or 5'-monophosphate is produced when the 5'- or 3'-phosphester linkage, respectively, is hydrolyzed, although no known exonuclease has been found to produce 3'-dNMPs. An example of a DNA exonuclease is E. coli Exonuclease I (Exo I) which digests ssDNA, possessing a free 3'—OH group, from the 3' to 5' direction to release single 5'-dNMPs in a stepwise manner, at a rate of ~100 to ~275 nucleotides per second (between ~31° C. to ~37° C., respectively).

Non-limiting examples of enzymes or exonucleases which could be utilized include the wild type or mutated form of Exonuclease 1, Exonuclease 2, Exonuclease 3, Exonuclease 5, Exonuclease 7, Exonuclease 8, Exonuclease T, Truncated exonucleases, modified exonucleases, mutant exonucleases, etc.

Non-limiting examples of methods for attaching a single exonuclease include expressing biotinylated exonucleases and then using linkers, and silane-based chemistry on the electrode; or engineering the exonuclease to contain a N-terminal cysteine residue, easily incorporated into the protein sequence, for thiol-based, site-specific immobilization. Any other suitable binding pair known in the art can be utilized to attach a single exonuclease enzyme to a surface of a device, where one member of a binding pair is attached to the exonuclease enzyme the other member of the binding pair is attached to a surface of the device (e.g., biotin/avidin, antibody/protein A and the like).

While certain of the figures herein depict the enzyme or exonuclease attached to the electrode at the bottom of the nanopore/nanowell, the enzyme or exonuclease could also be attached to the internal walls of the nanopore/nanowell, as long as there is spacing or clearance maintained between the transmembrane channel in the planar lipid bilayer and the enzyme or exonuclease.

Non-limiting examples of this spacing distance include 50 nm, 100 nm, 200 nm, 250 nm, 500 nm, 750 nm, 1 μm, 2 μm, 3 μm, 4 μm, 5 μm, 6 μm, 7 μm, 8 μm, and 10 μm.

As a specific example, exonuclease T (ExoT), which is a single-stranded DNA (ssDNA) exonuclease that is also active on ssRNA, releases NMPs in the 3' to 5' direction and cleaves ssRNA at a rate of 1 monophosphate every 3 to 300 ms. In this case, each individual NMP will escape the enclosed nanopore electrode volume with 100% efficiency and have its exact identity determined via a single pass or a high resolution multi toggle "read" in ~1.4 ms (depending on the exact nanopore electrode geometry and thus the total enclosed internal volume of the nanopore electrode, and the utilized experimental conditions), such that each NMP can be readily identified and released into the bulk solution long before the next NMP is released by the enzyme or exonuclease.

Figure 9:
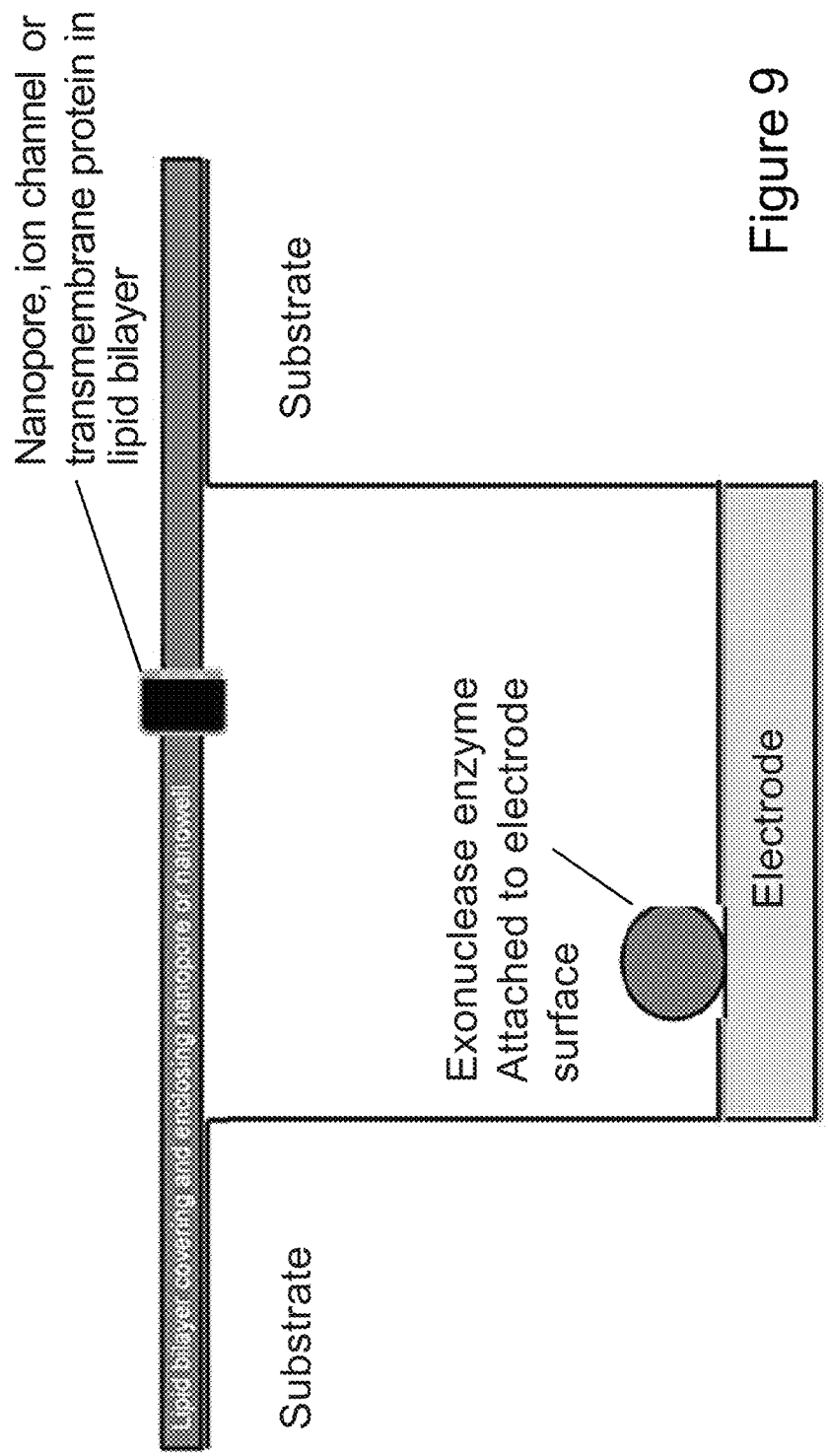
FIG. 9 shows an embodiment of a nanopore/nanowell electrode with an electrode at the bottom of the nanowell.
Figure 10:
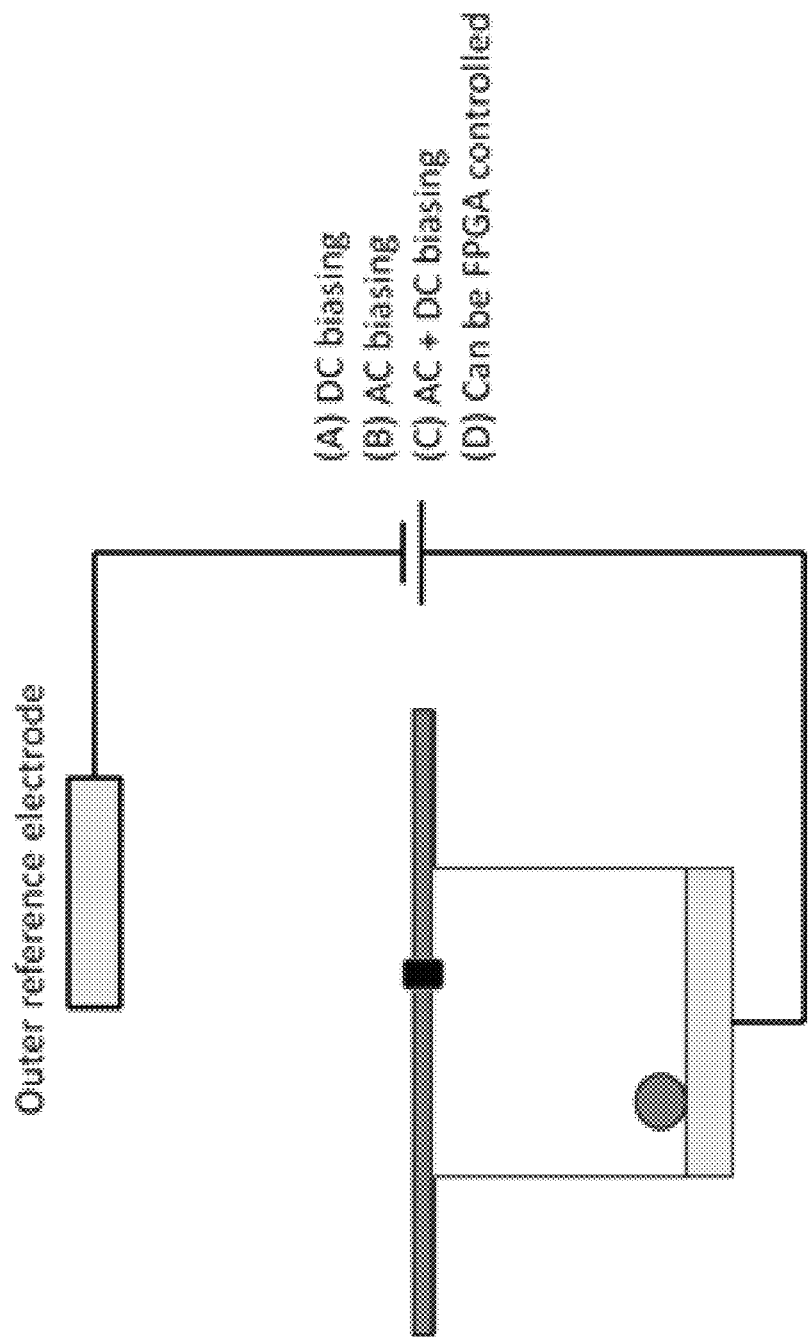
FIG. 10 shows an embodiment of a nanopore/nanowell electrode device in which both electrodes are illustrated.

Certain embodiments of a nanopore/nanowell device are illustrated in FIGS. 9 and 10.

A device and mechanism is provided for identifying individual monomeric units in sequential order as they are released or cleaved from a polymer strand via an enzyme which acts on the polymer. The polymer in solution is driven into and through the transmembrane channel of a membrane into a confined volume of solution that is enclosed by the membrane, the walls of a substrate supporting the membrane, and an electrode at the bottom of the confined volume. Once within the confined volume the polymer interacts with, is bound by, and is acted upon by the enzyme attached to the electrode at the bottom of the confined volume (e.g., the enzyme is attached to the electrode via a covalent attachment), cleaving monomeric units from the polymer one at a time from one end of the polymer to the other. As these monomeric units are cleaved from the polymer, by the enzyme, they diffuse around the confined volume until they reach the transmembrane channel in the membrane at which point they are driven back out of the confined volume, through the transmembrane channel, where their identity is determined, in the sequential order in which they are cleaved.

Sequencing

Also provided are methods for sequencing a polymer. Methods of sequencing can include using a device as described herein or one or more components of a device as described herein. In certain embodiments, a bulk solution is provided external to a chamber of a device having a confined volume; and a polymer to be sequenced is provided to the bulk solution. A polymer is driven electrophoretically and/or electroosmotically from a bulk solution through a transmembrane channel into a confined interior volume of a chamber. In some embodiments, a transmembrane channel is a biological nanopore, a solid state nanopore, an ion channel or a transmembrane protein. A polymer contacts an enzyme in a confined volume of a chamber, under conditions in which an enzyme cleaves monomeric units from a polymer. Monomeric units in the order which they are sequentially cleaved from a polymer by an enzyme are electrophoretically and/or electroosmotically driven out of a confined volume of a chamber through a transmembrane channel. The identity of each monomeric unit cleaved from a polymer is determined as a monomeric unit translocates through a transmembrane channel based on its current signature, translocation time, and/or associated current noise level modulation thereby determining the sequence of the polymer. In certain embodiments, the entire sequence of a polymer is determined. In certain embodiments, a portion of the sequence of a polymer is determined.

Polymers can be any of the polymers previously described, but are not limited to the described polymers. Typically, the polymer is single stranded RNA or single stranded DNA.

A monomeric unit can be, but is not limited to, a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide, In certain embodiments, a single polymer molecule is translocated into a confined volume of a chamber. In some embodiments, detection of a single translocation conductance spike confirms translocation of a single polymer molecule into a confined volume of a chamber. In some embodiments, after detection of a single translocation conductance spike, the voltage bias used to electrophoretically and/or electroosmotically drive a polymer into a confined interior volume of a chamber is decreased so that additional polymer molecules do not enter into a confined volume of a chamber.

In certain embodiments, an enzyme capture probability time can be determined. In some embodiments, an enzyme capture probability time can be determined experimentally, based on the period of time from detection of a translocation conductance spike of a polymer entering a confined volume of a chamber and detection of a change in conductance resulting from a first monomeric unit cleaved from a polymer translocating through a transmembrane channel out of a confined volume of a chamber. In some embodiments, a capture time or capture efficiency of a transmembrane channel is removed from the above discussed period of time. In some embodiments, an enzyme capture probability time is about 1 microsecond to about 10 minutes, about 500 microseconds to about 5 minutes about 1 millisecond to about 1 minute, about 500 milliseconds to about 1 minute, about 1 second to about 1 minute or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 120, 240, or 360 seconds.

In certain embodiments, electrophoretically and/or electroosmotically driving a monomeric units out of a confined volume of a chamber through a transmembrane channel occurs after an enzyme capture time probability. In some embodiments, electrophoretically and/or electroosmotically driving a monomeric unit out of a confined volume of a chamber through a transmembrane channel comprises reversing drive bias polarity.

In certain embodiments, a monomeric unit, after being cleaved or released from the polymer, encounters and translocates through a transmembrane channel in a period of time less than or equal to a maximum operating frequency of the enzyme. Maximum operating efficiency of an enzyme is the maximum rate of a reaction that an enzyme catalyzes. For example, for a nuclease it is the highest rate or frequency at which nucleotides are cleaved from a polynucleotide (e.g. ExoT cleaves ssRNA at a rate of one monophosphate every 3 to 300 milliseconds).

In certain embodiments, a monomeric unit encounters and translocates through a transmembrane channel within about 10 microseconds to about 5 seconds, about 100 microseconds to about 1 second, about 500 microseconds to about 500 milliseconds, about 1 millisecond to about 300 milliseconds or about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 milliseconds.

In certain embodiments, an aqueous solution of a buffered electrolyte or of an ionic solution, as previously described, is provided to the interior of a confined chamber.

In certain embodiments, the viscosity of an aqueous solution of a buffered electrolyte or of an ionic solution is increased or decreased to a level that increases capture efficiency and/or measurable resolution of a polymer or monomeric unit by a transmembrane channel.

In certain embodiments, methods of sequencing a polymer or portion thereof can include for each monomeric unit a multi-pass toggling routine by which a monomeric unit is passed back and forth numerous times through a transmembrane channel. In certain embodiments, a monomeric unit cleaved from a polymer is electrophoretically and/or electroosmotically driven out of a confined volume of a chamber through a transmembrane channel. Upon detection of a translocation of the monomeric unit through a transmembrane channel, a reversal of DC drive bias is triggered so that the monomeric unit is electrophoretically and/or electroosmotically driven back through a transmembrane channel into a confined volume of the chamber. Upon detection of another translocation of the monomeric unit through the transmembrane channel, a reversal of DC drive bias is triggered to electrophoretically and/or electroosmotically drive the monomeric unit back through a transmembrane channel out of a confined volume of a chamber. In certain embodiments, the above described routine of driving a monomeric unit through a transmembrane channel into and out of a confined volume is repeated multiple times. In certain embodiments, multiple times can be, but is not limited to, about 2 times to about 200 times, about 5 times to about 100 times, about 10 times to about 50 times, about 10 times to about 20 times or about 5, 6, 7, 8, 9, 10, 11, 12, 13, 14, 15, 16, 17, 18, 19, 20, 21, 22, 23, 24 or 25 times. In some embodiments, the number of times a monomeric unit is passed back and forth through a transmembrane channel is the number of times required to determine a mean translocation/blocking level of the monomeric unit, determine a mean translocation time for the monomeric unit translocating through the transmembrane channel, and/or determine a mean current noise level modulation imparted by the monomeric unit translocating through the transmembrane channel, which allows for differentiation from other monomeric units and identification of the monomeric unit.

In some embodiments, the routine is carried out for a first monomeric unit cleaved from a polymer and then carried out repeatedly, in sequential order for the other monomeric units cleaved from a polymer.

In some embodiments, prior to repeating the above routine in order to identify a next monomeric unit cleaved from a polymer, the previously identified monomeric unit is released into the bulk solution (e.g., driven out as part of the voltage routine) and the drive bias is reset in order to drive the next monomeric unit out of the confined volume. After the identification of the next monomeric unit cleaved from the polymer the process is repeated until monomeric units representing the entire sequence of the polymer are identified or a number of monomeric units representing a desired portion of the sequence are identified.

In certain embodiments, for methods of sequencing a polymer or portion thereof, after a first translocation event is detected for a monomeric unit (e.g. by observing a translocation conductance spike), it is not necessary to detect subsequent translocation events for that monomeric unit as an indicator of the time to trigger a reversal of DC drive bias. Once a first translocation event for a monomeric unit is detected, a timing routine can be used for toggling the voltage (reversal of DC drive bias) so that the monomeric unit moves back and forth through the transmembrane channel. The triggering of a reversal of DC drive bias can occur automatically based on a predetermined period of time. In some embodiments, a reversal of DC drive bias is automatically triggered after a period of time of about 5 microseconds to about 500 microseconds, or about 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 microseconds.

Figure 1B:
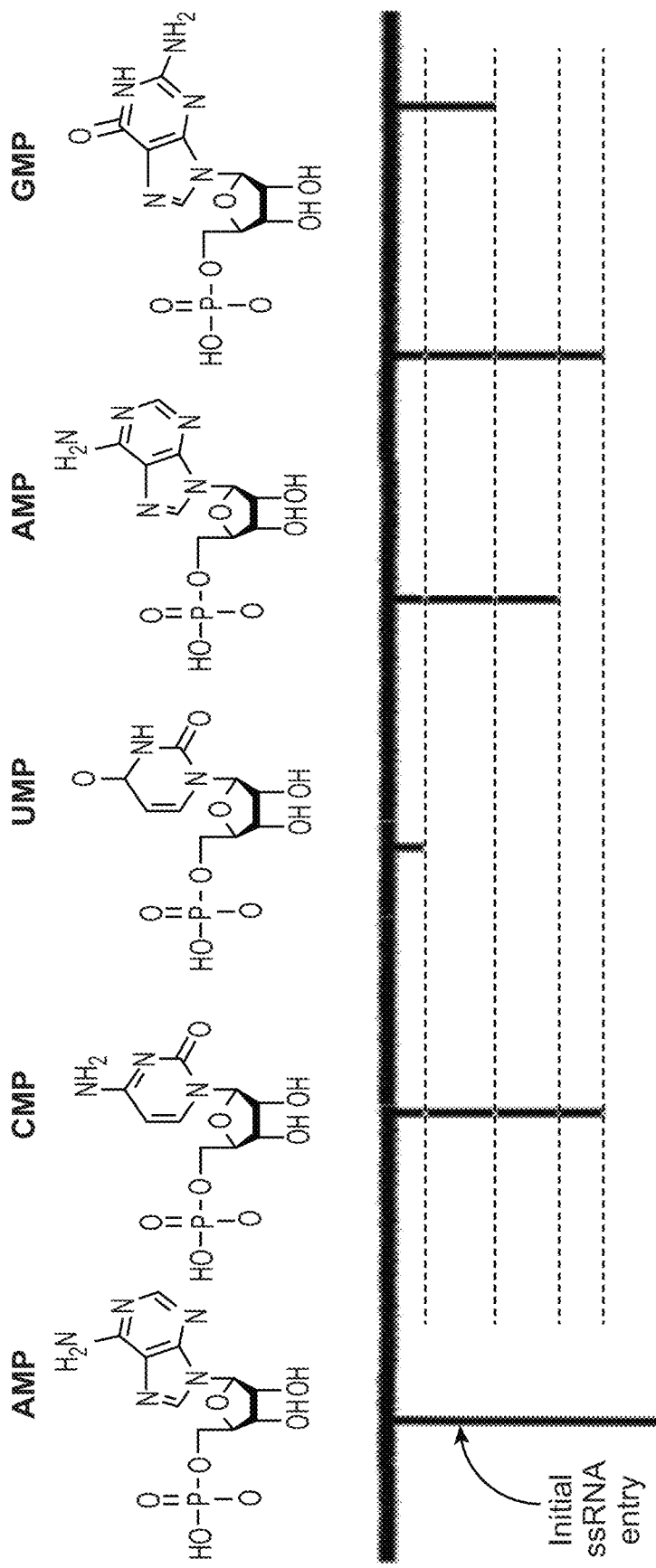

In the Nanopore/Nanowell Electrode Enabled Exonuclease Sequencing method, conceptualized in FIGS. 1A and 1B (for RNA). FIG. 1A depicts the associated platform (not drawn to scale).

FIG. 1B depicts the theoretical current as a function of time trace workflow associated with first capturing ssRNA inside of the nanopore electrode and then determining the identity of each nucleotide monophosphate (NMP) as it exits in sequential order after being sequentially cleaved/released by the surface bound exonuclease (ExoT). A gold nanopore/nanowell electrode is utilized (i.e. a recessed gold electrode at the bottom of a nanopore or nanowell within a substrate that partially enclosing a solution volume directly above the electrode, which is in contact with a solution volume outside of the volume partially enclosed by the nanopore or nanowell electrode). The opening aperture of the nanopore/nanowell electrode or partially enclosed volume, is capped with a synthetic planar lipid bilayer (PLB) to fully enclose the volume of solution within the nanopore electrode. This PLB contains a single transmembrane channel (i.e. a biological nanopore, ion channel, transmembrane protein, etc.) engineered for enhanced or optimal nucleotide monophosphate (NMP) or monomeric unit differentiation. Inside of the nanopore electrode, covalently attached to the gold surface, is a single enzyme or exonuclease which is attached prior to PLB formation and transmembrane channel insertion into the PLB. This enzyme or exonuclease works by cleaving monomeric units or nucleotides one at a time from the end (exo) of a polymer or polynucleotide chain. A hydrolysis reaction that breaks phosphodiester bonds at either the 3' or the 5' end occurs.

In order to initiate sequencing, a single strand of a polymer (single stranded DNA, single stranded RNA, etc.) is electrophoretically driven from the bulk sampling solution down through the transmembrane channel in the PLB, into the confined volume of the nanopore/nanowell electrode, as determined via a single entering translocation conductance spike, measured in the current as a function of time plot of the transmembrane channel (FIG. 1B). The associated voltage drive bias, used to capture the polymer inside of the nanopore electrode, is then decreased in order to prevent any further polymer captures. After an experimentally determined enzyme or exonuclease capture probability time, the drive bias polarity is reversed in order to drive the diffusion/migration of cleaved/released monomeric units, NMPs, that the enzyme or exonuclease is about to begin releasing, back out of the nanopore electrode via the transmembrane channel in the PLB. The identity of the monomeric unit or NMP exiting the channel is determined, in the order in which it is cleaved or released by the enzyme or exonuclease, by the change in conductance of the channel which is imparted by monomeric unit or NMP as it translocates through the transmembrane channel.

Figure 2A:
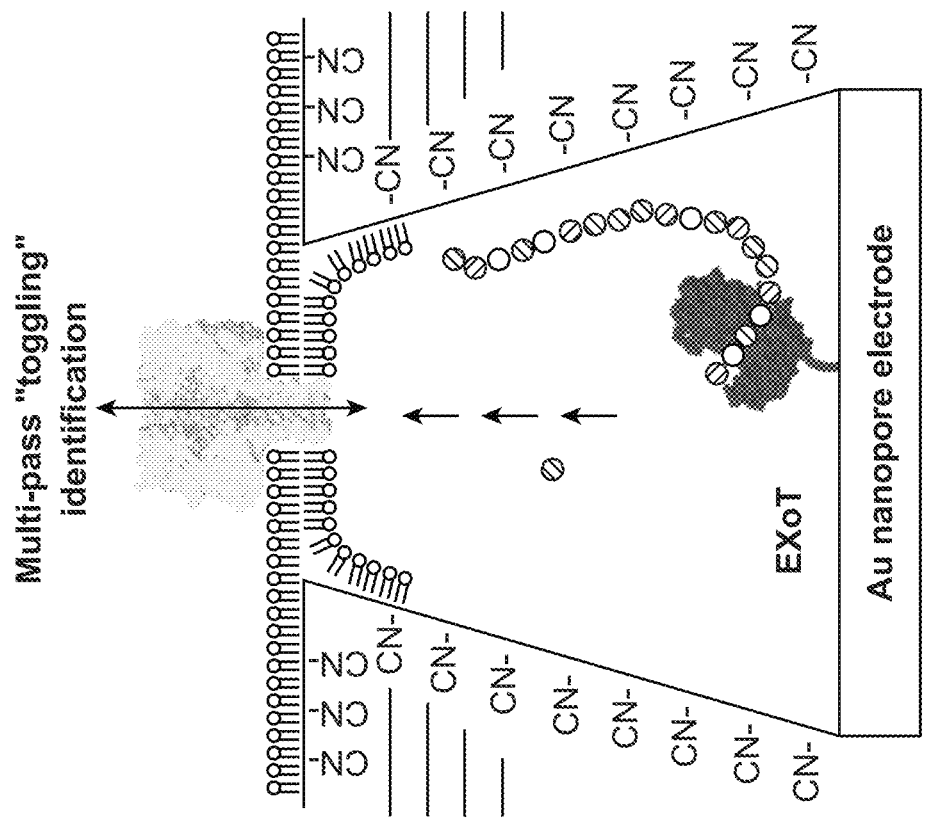
FIGS. 2A and 2B represent a conceptualization of the direct RNA Nanopore/Nanowell electrode sequencing (RNA-NES) concept using a multi-pass "toggling" assessment.
Figure 2B:
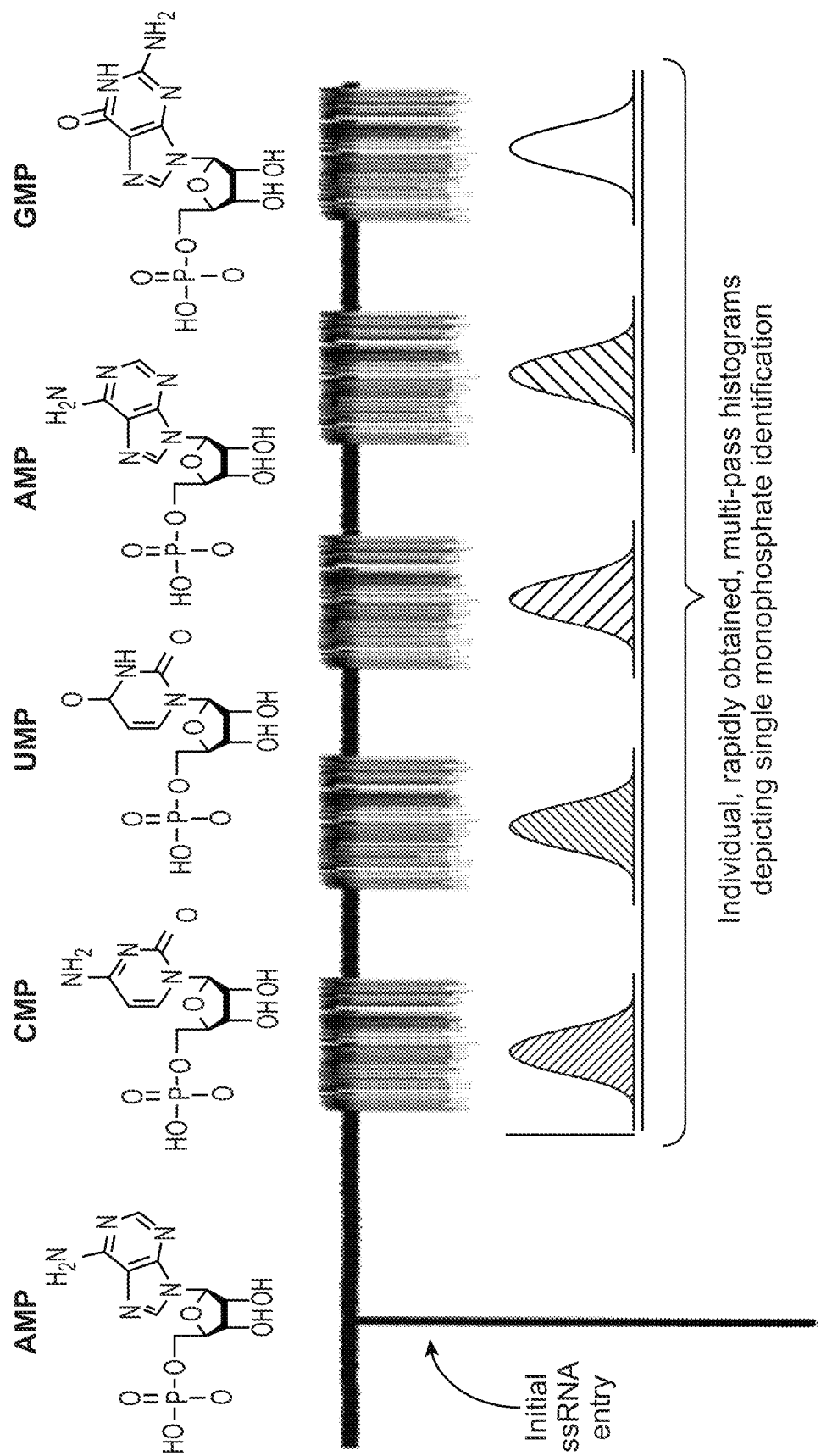

If the identity of the monomeric unit or NMP is not readily determined by this single translocating event, associated with the monomeric unit or NMP exiting the enclosed nanopore electrode volume through the transmembrane channel, as determined via a smaller conductance exit translocation spike relative to the entry conductance spike associated with the polymer entering the nanopore electrode (see FIG. 1A), the NMP will be rapidly multi-passed or "toggled" back and forth through the channel, as depicted in FIGS. 2A and 2B, via FPGA controlled high speed DC biasing capabilities, in order to determine the precise mean translocation/blocking level of that NMP and thus its identity with extremely high resolution, before releasing it into bulk solution outside of the nanopore electrode. At which point the drive bias will be reset in order to drive the next to be released NMP out of the nanopore electrode. This process will be carried out repeatedly, in sequential order, until the captured polymer strand is read to completion. FIG. 2a shows the platform for the direct RNA Nanopore/Nanowell electrode sequencing (RNA-NES) concept. FIG. 2B depicts the theoretical current as a function of time trace workflow associated with first capturing ssRNA inside of the nanopore electrode and then determining the identity of each nucleotide monophosphate, via a multi-pass "toggling" assessment, as they are sequentially cleaved/released by the surface bound exonuclease (ExoT).

Furthermore, the utilization of a multiplexed platform, in which multiple nanopore/nanowell electrodes are utilized simultaneously for this specific application, will enable relatively high throughput and reasonable sample characterization times.

Non-limiting examples of features of the Nanopore/Nanowell Electrode Enabled Exonuclease Sequencing device and associated mechanism are: (1) The confinement of the exonuclease enzyme within a volume such that any polymer interacting with or being acted upon by the exonuclease enzyme has to first translocate through the transmembrane channel of the PLB to reach the exonuclease enzyme. This ensures only one polymer molecule is acted upon or sequenced at a time and provides a mechanism to determine when to start reading or sequencing the monomers that will be released by the exonuclease enzyme. It also ensures that the only thing that would be translocating the transmembrane channel during the reading or sequencing is the single polymer that has entered the volume and its associated monomers or NMPs that are being released and electrophoretically driven out of the confined nanopore/nanowell volume, not other polymers or other monomers in the bulk sampling solution. (2) The separation in spacing (i.e. the clearance) of the transmembrane channel and the exonuclease enzyme, such that the free end of the polymer that the exonuclease enzyme is acting on and cleaving does not get electrophoretically pulled back into the transmembrane channel and disrupt the ability to determine the identity and sequence the monomers or NMPs that the exonuclease is releasing. Non-limiting examples of the spacing distance between the transmembrane channel and the exonuclease enzyme include about 50 nanometers to about 10 micrometers (e.g., a spacing distance of about 50 nm, 100 nm, 200 nm, 250 nm, 500 nm, 750 nm, 1 µm, 2 µm, 3 µm, 4 µm, 5 µm, 6 µm, 7 µm, 8 µm, and 10 µm). (3) The confinement of the monomers or NMPs that the exonuclease enzyme is releasing such that they cannot diffuse away from the transmembrane channel. (4) The confinement of the monomers or NMPs that the exonuclease is releasing such that they will diffuse around that confined volume and encounter and translocate the transmembrane channel within a set period of time (e.g., in less than about 100 microseconds to about 300 milliseconds (e.g., less than about 100 µs, 1 ms, 5 ms, 10 ms, 50 ms, 100 ms, 200 ms, 300 ms)) after being cleaved or released by the exonuclease enzyme. (5) The multi-passing, toggling or flossing of the monomers or NMPs through the transmembrane channel such that as multiple measurements of this translocation process are made on a single molecule basis, the distribution of measured blocking or translocation values for individual translocation or pass approach a normal distribution, based on the Central Limit Theorem, gathered about a mean value ($\bar{x}$) with a standard deviation ($\sigma$). Consequently, the effect of the variability in the physical process of translocation (i.e. the variability in the monomer's path, velocity, and orientation), and thus the $\sigma$ of the measurement, is systematically reduced with more measurements to provide a very precise value of $\bar{x}$. This multi-pass, toggling, or flossing approach can be used to measure the precise value of $\bar{x}$ of any molecule translocating or passing through a transmembrane channel, Non-limiting examples of these molecules include an analyte, organic molecule, inorganic molecule, amino acid, peptide, polypeptide, nucleotide monophosphate, nucleoside monophosphate, ribonucleic acid, deoxyribonucleic acid, ribonucleotide, deoxyribonucleotide, monomeric unit of a polymer, or other unit of a polymer. The key to being able to multi-pass, toggle, or floss a molecule through a transmembrane channel as opposed to a synthetic nanopore or channel is being able to resolve (either in the DC conductance current signature of the transmembrane channel or the AC conductance current signature of the transmembrane channel) and trigger the DC bias reversal off of the very fast, sub ms, translocation events.

The transmembrane channel utilized to determine the identity of the monomeric units or NMP being released by the enzyme or exonuclease can be a biological nanopore, ion channel, or transmembrane protein and be either the wild type form or a mutated, engineered, and/or chemically modified form. Non-limiting examples of transmembrane channels which could be utilized include alpha-hemolysin (αHL), aerolysin, *Mycobacterium smegmatis* porin A (MspA), *Escherichia coli* CsgG, and outer membrane protein F (OmpF).

Non-limiting examples of transmembrane channel mutations which are anticipated to increase the contrast between monomeric units or NMPs as they translocate through the channel include a reduction of negative charge within the channel, an increase in the positive charge within the channel, a reduction in overall channel charge (increasing the hydrophobicity), a reduction in the cross sectional width of a channel (via amino acid size and/or chemically associated molecular adaptors), an elongation of the "sensing zone" of the channel, the incorporation of electrostatic or van der Waal traps within the channel or sensing zone, and the like, or a combination thereof.

Furthermore, the entrance of the transmembrane channel (exposed to the solution outside of the nanopore electrode) or the exit of the channel (exposed to the solution inside of the nanopore electrode), often referred to by those familiar with the art as cis and trans, respectively, can be mutated (opened up or have their charge altered) as a means of either enhancing the capture efficiency (reducing the energy barrier to entry) of the polymer or escape efficiency (reducing the energy barrier to exit) of the cleaved monomeric unit or NMP, or both.

While the nanopore/nanowell electrode shown in FIGS. 1A and 2A herein depict a conical geometry, any nanopore electrode geometry would be acceptable including but not limited to conical, cylindrical, cubical, triangular, cuboidal, etc. Examples of a conical or cubical geometry are depicted in FIGS. 9 and 10.

While the nanopore/nanowell electrode shown in the figures herein depict a Au electrode at the bottom of the nanopore electrode, other suitable electrode materials and combinations thereof would be acceptable. Non-limiting examples of electrode materials include Au, Ag, Ag/AgCl, Pt, the like, and combinations thereof. For instance a gold nanodisk or hemispherical electrode surrounded by a Ag/AgCl ring electrode could be utilized.

The nanopore/nanowell electrode substrate itself can be but is not limited to being fabricated in glass, quartz, sapphire, graphene, $SiO_2$, SiN, $Si_3N_4$, photoresist, SU8 photoresist, polyimide, kapton, alumina, fused silica, alumina oxide, polymer, metal, etc.

The nanopore electrode can be fabricated by any means know to those familiar with the art. Non-limiting examples include benchtop fabrication, nanofabrication methods and lithography based methods.

The nanopore/nanowell electrode substrate can be chemically modified in order to aid in the ability to wet the inside of the nanopore electrode, alter the electrical properties of the substrate, aid planar lipid bilayer formation and stability, limit or prevent non-specific adsorption, and/or alter or remove the charge associated with the walls of the substrate. While a cyano-silane is depicted in FIGS. 1A and 2A as the surface coating, any suitable silane coating, neutral coating, charged coating, hydrophilic coating, omniphobic coating, etc., formed chemically, via atomic deposition, or by any other means can be utilized.

Methods of Identification

Also provided are methods for identification of molecule by multi-pass toggling a molecule through a transmembrane channel by rapidly reversing DC drive bias. A transmembrane channel can be a biological nanopore, a synthetic nanopore, an ion channel or a transmembrane protein. In some embodiments a molecule is an organic molecule, an inorganic molecule, an amino acid, a modified amino acid, a protein, a modified protein, a protein fragment, a modified protein fragment a peptide, a modified peptide, a polypeptide, a modified polypeptide, an antibody, an antigen, an antigen bound antibody, a cell, an extracellular vesicle, a polymer, a nucleotide monophosphate, a modified nucleotide monophosphate, a nucleoside monophosphate, a modified nucleoside monophosphate, a ribonucleic acid, a deoxyribonucleic acid, a ribonucleotide, a deoxyribonucleotide, a modified ribonucleotide or a modified deoxyribonucleotide.

In certain embodiments, steps of driving a molecule back and forth through a transmembrane channel is repeated multiple times. In certain embodiments, multiple times can be, but is not limited to, about 2 times to about 200 times, about 5 times to about 100 times, about 10 times to about 50 times, about 10 times to about 20 times or about 5, 6, 7, 8, 9, 10, 11, 12, 13, 14, 15, 16, 17, 18, 19, 20, 21, 22, 23, 24 or 25 times. In some embodiments, the number of times a molecule is passed back and forth through a transmembrane channel is the number of times required to determine a mean translocation/blocking level of the molecule, determine a mean translocation time for the molecule translocating through the transmembrane channel, and/or determine a mean current noise level modulation imparted by the molecule translocating through the transmembrane channel, which allows for differentiation from other molecules and identification of the molecule.

In certain embodiments, for methods of identifying a molecule, after a first translocation event is detected for a molecule (e.g. by observing a translocation conductance spike), it is not necessary to detect subsequent translocation events for the molecule as an indicator of the time to trigger a reversal of DC drive bias. Once a first translocation event for a molecule is detected, a timing routine can be used for toggling the voltage (reversal of DC drive bias.) so that the molecule moves back and forth through the transmembrane channel. The triggering of a reversal of DC drive bias can occur automatically based on a predetermined period of time. In some embodiments, a reversal of DC drive bias is automatically triggered after a period of time of about 5 microseconds to about 500 microseconds, or about 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 microseconds.

Solution Composition

The associated method for determining the sequence of a polymer can be carried out in an aqueous solution composed of a buffered electrolyte and/or an ionic solution. Non-limiting examples electrolytes that could be utilized include KCl, NaCl, LiCl, ionic liquids, etc. buffered anywhere from pH 3.5 to 10.5 or within an unspecific usable range associated with the substrate and/or channel.

A standard electrolyte condition for exonuclease activity, is in 67 mM glycine-KOH (pH 9.5), 6.7 mM $MgCl_2$, 10 mM 2-mercaptoethanol at 37° C. However, Exo I is stable under a variety of conditions, including the incorporated electrolyte; Myler et al. demonstrated Exo I activity in 60 mM NaCl, while Clarke et al. demonstrated Exo I activity in 200 mM to 800 mM KCl.

Furthermore, electrolyte additives can be added to increase the viscosity of the solution to help control diffusion of the monomeric unit or NMP within the confined volume of the nanopore/nanowell electrode. Non-limiting examples of viscosity increasing additives include potassium glutamate, poly ethylene glycol, glycerol, etc.

EXAMPLES

The examples set forth below illustrate certain embodiments and do not limit the technology.

Example 1: Feasiblity of Detection/Differentiation of 5'-NMPs

Figure 3A:
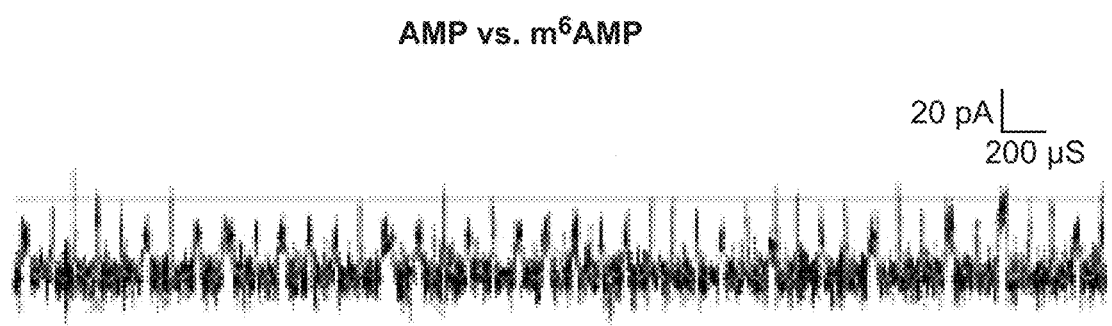
FIGS. 3A and 3B show the detection/differentiation of AMP vs. M$^6$AMP.
Figure 3B:
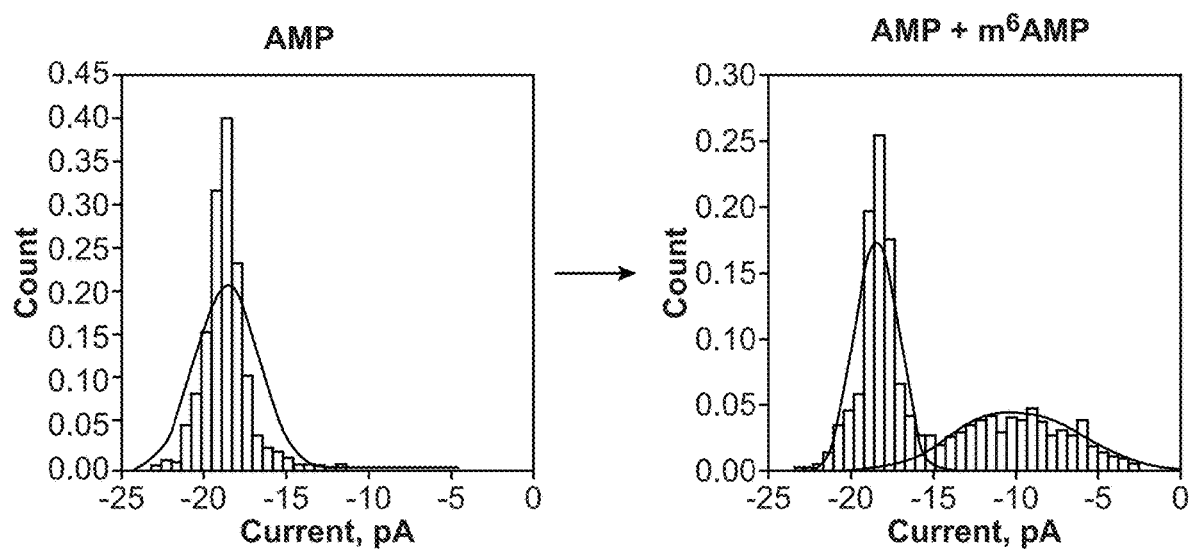

Due to the small and highly charged nature of a monomeric unit or NMP, most wild type transmembrane channels are not ideally suited for identifying and differentiating them as they transloate through, due to the NMP's inability to modulate the conductance of the nanopore above the background open pore noise level and/or to modulate the conductance in a way that is distinguishable from other various monomeric units or NMP types. However, mutant αHL pores that are capable of detecting/differentiating 5'-NMPs have been generated. FIGS. 3A and 3B depict the proof-of-concept detection/differentiation of adenosine monophosphate (AMP) vs. $N^6$-methyladenosine 5'-monophosphate ($m^6AMP$) using the mutant αHL M113K. FIG. 3A represents current as a function of time traces for AMP vs. $M^6AMP$. FIG. 3B represents the associated translocation current blocking level histograms for the detection/differentiation AMP vs. $M^6AMP$ (100 kHz black curve (left), 10 kHz red curve (right)). All data were collected in 800 mM KCl, 10 mm Tris (pH 7.2), at 20° C. using a 50 mV bias. These general data demonstrate the initial feasibility of an αHL pore's ability to detect/differentiate 5'-NMPs; a requirement of the Nanopore/Nanowell Electrode Enabled Exonculease method.

Example 2: Feasibility of Nucleotide-by-Nucleotide Sequencing Using an Exonuclease in a Finite Volume The feasibility of performing nucleotide-by-nucleotide sequencing using an exonuclease within a finite volume was assessed by calculating the distribution of capture times following the cleavage of a single nucleotide. The time distribution of the probability density function (PDF) was first calculated, which describes the time varying likelihood of finding a nucleotide at a particular location. This distribution is calculated by solving the Fokker-Plank equation (eq. 1) for the PDF, $$\frac{\partial P}{\partial t} = \nabla \left( D\nabla P + \frac{zF}{RT} DP\nabla\phi - uP \right) \quad (1)$$

The second and third terms in the gradient expression, which relate to the migrative and convective components of the flux, were set to zero as there is no electric field except within the 'collection zone' (vide infra) and there is negligible fluid flow possible within the sealed volume. Equation 1 thus simplifies to $$\frac{\partial P}{\partial t} = D\nabla^2 P \quad (2)$$

Where $D=3\times10^{-5}$ cm$^2$/s is the diffusion coefficient of a single nucleotide. Without loss of generality, it was assumed that the geometry was axially symmetric with the exonuclease and αHL lying on the axis of rotation. A 2D slice from the axis that represents the geometry where the equations were solved is shown in FIG. 4. FIG. 4 is a schematic of the finite element model used for testing the feasibility of nucleotide-by-nucleotide sequencing using an exonuclease in a confined volume (not to scale).

The initial condition was of uniform probability density in a 5 nm ball (orange hemisphere labelled "initial release point" in FIG. 4, size exaggerated), where the value was chosen to integrate to 1 and zero likelihood of finding the nucleotide elsewhere. This approximates a Dirac delta function, i.e., the nucleotide starts precisely where it released from the exonuclease.

On all boundaries except that labelled "collection zone" in FIG. 4, a no normal flux boundary condition was applied $$0 = -D\nabla P \cdot \bar{n} \qquad (3)$$

where $\bar{n}$ represents the inward pointing unit normal to the surface.

The boundary labelled "collection zone" in FIG. 4 (size exaggerated) represents the radius after which the electric field is guaranteed to drive the nucleotide into the nanopore. This 'point of no return' for the nucleotide is represented by an absorbing boundary condition.

$$P=0 \qquad (4)$$

Note, the radius of this zone is a function of several parameters, including the temperature, diffusion coefficient and applied potential. The value of 5 nm is used for the numerical simulations presented herein as it is a value that can be plausibly achieved through adjusting experimental parameters.

Solution of the problem was achieved through using the finite element method implemented using the commercial package Comsol Multiphysics version 5.2a.

The integral of the flux probability density through the collection zone, J, represents the likelihood that a nucleotide would be captured during a period of time. This is calculated by the following integral that is performed as an integral of rotation.

$$J = \int_{\text{collection zone}} D\nabla P \cdot \bar{n} \qquad (5)$$

Simulation Results

Figure 5:
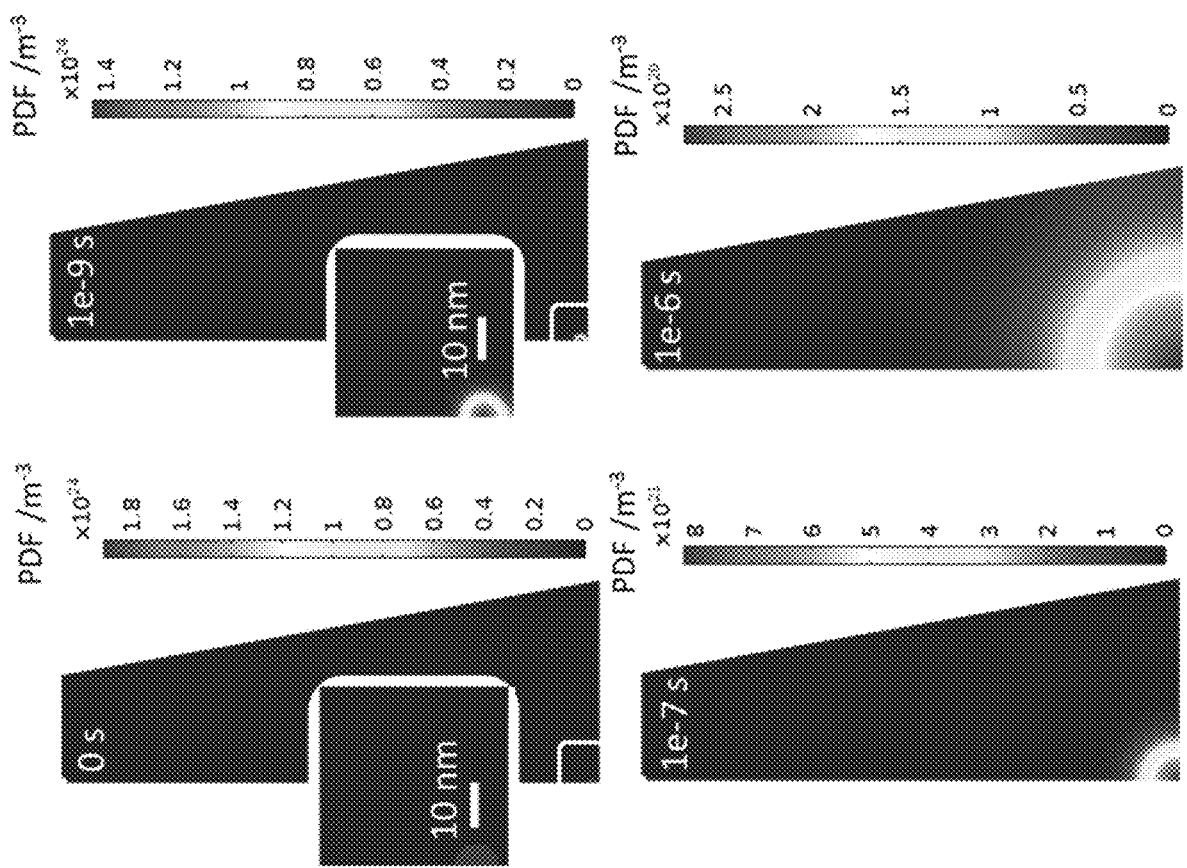
FIG. 5 shows a PDF distribution shortly after nucleotide release, showing rapid radial expansion. Insets show region of nucleotide release (white box).

As soon as the nucleotide is released it begins a random walk within the pore. Initially the probability density function spreads out radially, meaning that the most likely place to find the nucleotide is close to where it was released. The region in which one is likely to find the nucleotide increases with time. FIG. 5, which plots the probability density in the first microsecond after release, shows precisely this. PDF distribution shortly after nucleotide release show rapid radial expansion (see FIG. 5). Insets show region of nucleotide release (white box). Note, in each part, the scale is chosen such that the maximum value of the PDF is shown in dark red. The radius at the top of the image is 100 nm and the depth of the pore is 0.5 μm.

Figure 6:
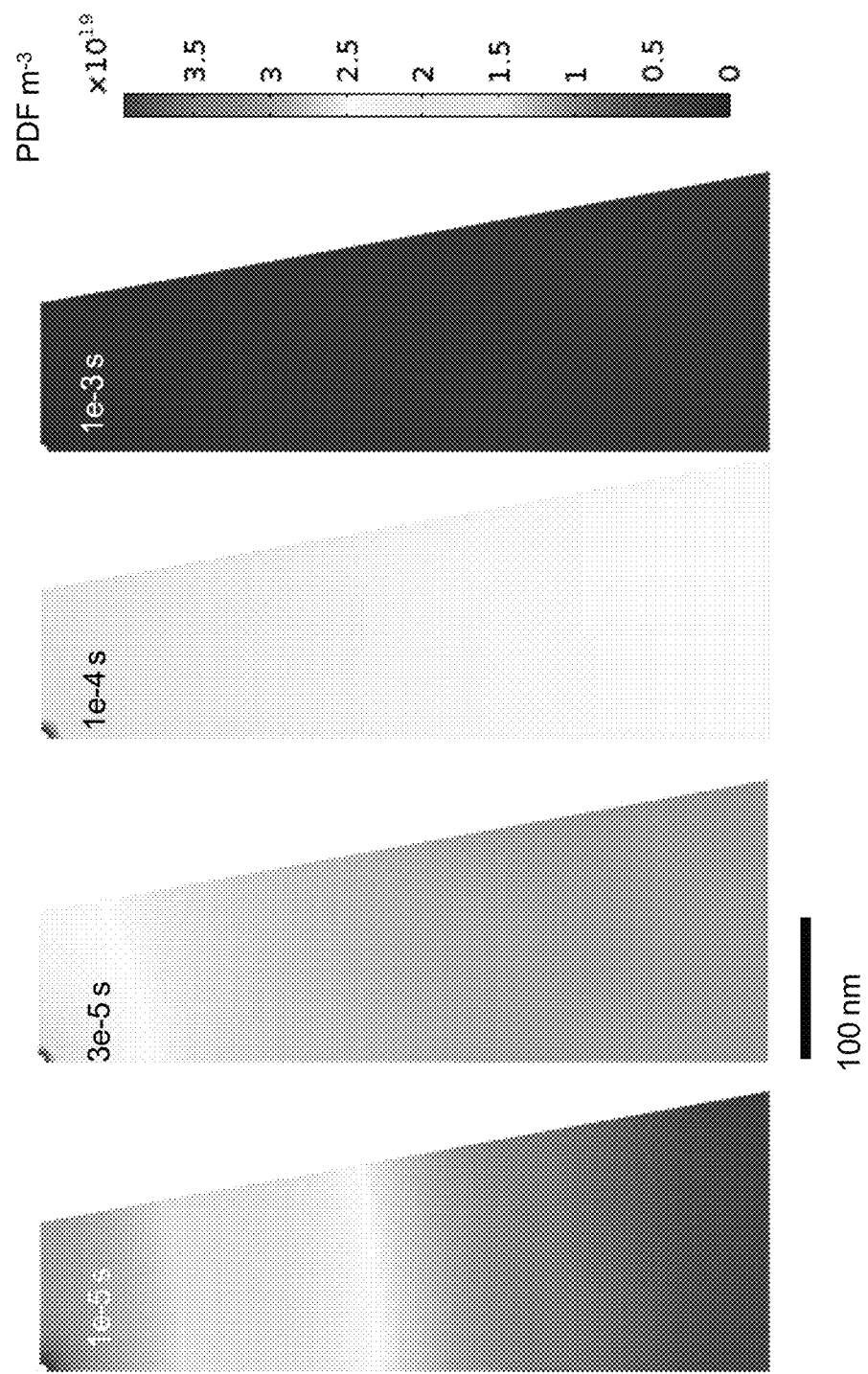
FIG. 6 shows PDF distribution as a function of time.

By ~10 μs the PDF has spread out, such that the likelihood of finding the nucleotide anywhere within the pore (except in the immediate vicinity of nanopore) is essentially uniform. The time dependent PDF at these later times is shown in FIG. 6. FIG. 6 shows PDF distribution as a function of time which shows that over ~1 ms the probability of the nucleotide remaining in the pore not having entered the αHL tends to zero. In this time range (10 μs-1 ms) the dominant effect is the capture of the nucleotide by the αHL, which lowers the probability of finding a nucleotide anywhere within the pore. By 1 ms the chance of finding a nucleotide within the pore is close to zero, or to put it another way, by 1 ms it is almost certain that the nucleotide has been captured and thus measured. PLB radius 100 nm, pore depth 0.5 μm, pore half-angle 10°, αHL collection radius 5 nm.

Figure 7A:
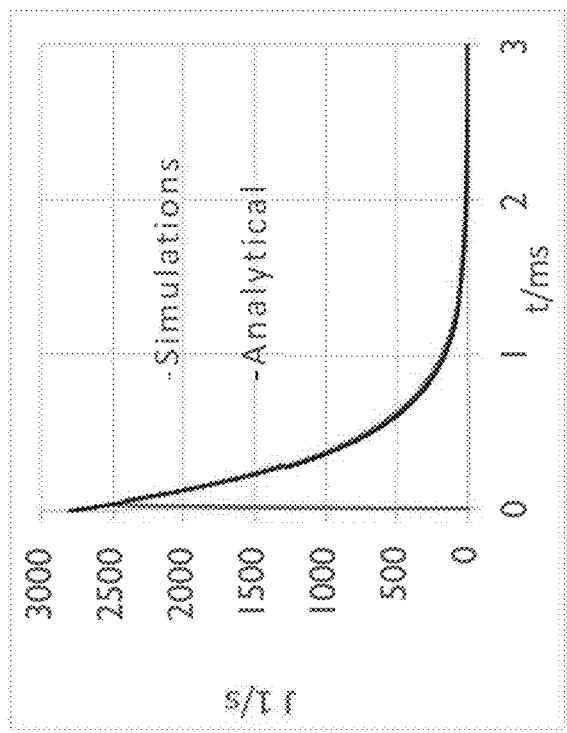
FIGS. 7A and 7B show the integrated flux passing through the αHL, J, (FIG. 7A) and the collection efficiency (CE) (FIG. 7B) versus time.

It is possible to state the likelihood of the capture more quantitatively by studying the integrated flux coming from equation 5. The nucleotide was released at the bottom of a 0.5 μm deep pore, 10° half-angle and 100 nm radius PLB. The integrated flux passing through the αHL, J, which is plotted versus time in FIG. 7A (red line, left-hand plot), shows that the likelihood of nucleotide capture by αHL rises rapidly at very short times (<<1 ms) and then decays in an exponential fashion with time. The reason for the decay is that with time it is less and less likely that there is still a nucleotide in the pore to be captured (i.e. it has already been captured, identified, and returned to bulk solution). We can calculate the capture efficiency (CE), that is the likelihood that the particle has been captured at time T by a further integral $$CE(T) = \int_0^T J(t)dt \qquad (6)$$

Figure 7B:
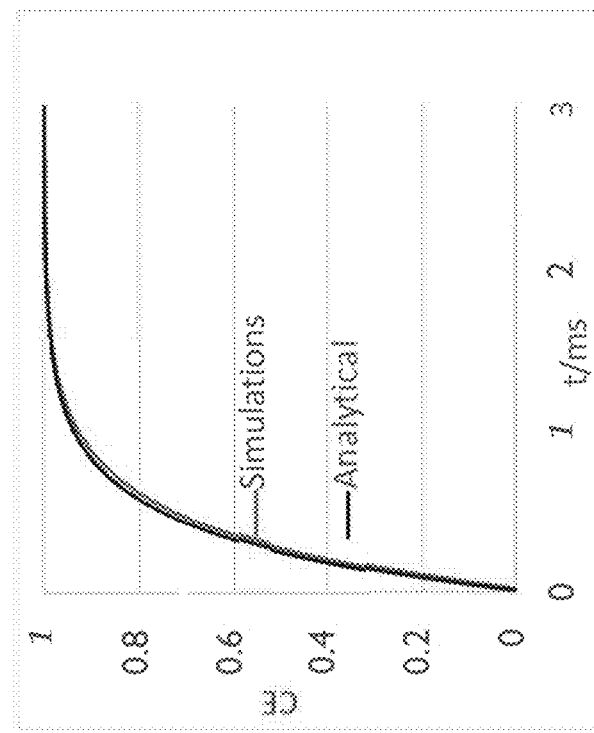

This quantity versus time is plotted in the right-hand part of FIG. 7B. This plot shows that by 1 ms it is ~95% certain that the nucleotide has been detected.

An Analytical Description

The inference that the decay in the flux is exponential can by founded analytically as follows.

First, we make the observation that for all but the shortest times the PDF is effectively uniform across the entirety of the pore. We define this quantity $\bar{P}$ and make the observation that at t=0 this should take the value 1/Vol where Vol is the volume within the nanopore/nanowell electrode. Next we make the observation that the flux to the □HL is closely approximated by the flux to a hemispherical electrode in an infinite plane, as long as the collection zone is small relative to the bilayer width, which should always be the case. Thus J can be written as $$J = 2\pi a D \bar{P} \qquad (7)$$

where a is the radius of the collection zone. Thus we can write the following differential equation describing how $\bar{P}$ varies with time $$\frac{d\bar{P}}{dt} = -\frac{2\pi a D \bar{P}}{Vol} \qquad (8)$$

the solution to this differential equation is $$P = \frac{\tau^2}{Vol.} \exp(-t/\tau) \qquad (9)$$

where we have $$\tau = Vol/2\pi a D. \qquad (10)$$

this can be substituted back into the equation for flux (Eq. 7) to give $$J=\tau \exp(t/\tau) \quad (11)$$

Performing the integral described by equation 6 to this expression gives the capture efficiency as $$CE=1-\exp(-t/\tau) \quad (12)$$

Analytical expressions in the top (FIG. 7A) and bottom (FIG. 7B) plots are Equations 11 and 12, respectively. Equations 11 and 12 are plotted as black lines alongside numerical simulations in FIGS. 7A and 7B, from which it is clear they excellently agree for all but the shortest times. Thus we can use τ as the frequency characteristic of the collection efficiency. For the truncated cone geometry shown (tip 100 nm radius, height 0.5 µm, 10° half-angle) the volume of the cone is ~3.4×10$^7$ nm$^3$, which gives a time constant of to τ=3.6×10$^{-4}$ s.

Capture Efficiency as a Function of Geometry

Figure 8:
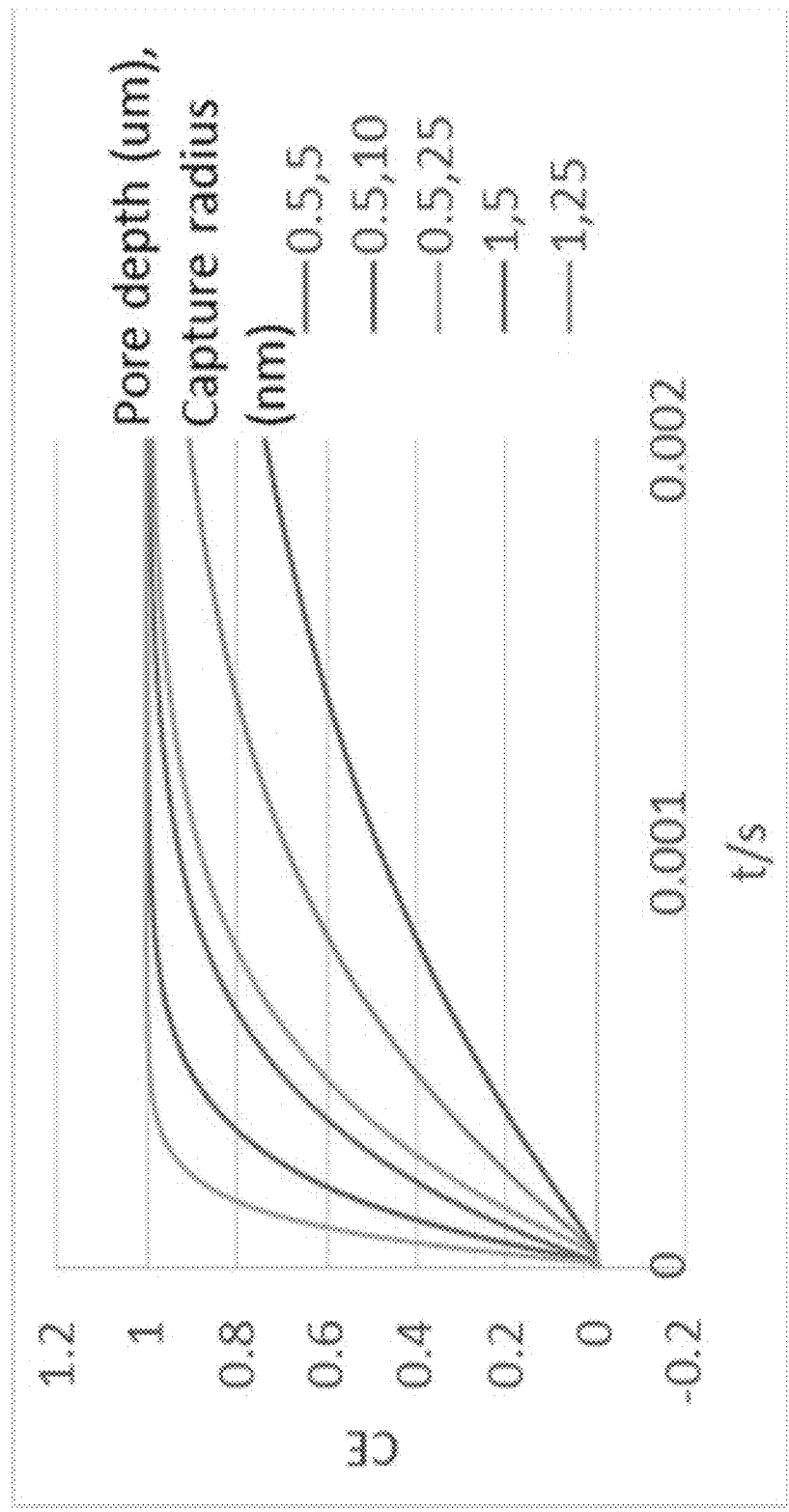
FIG. 8 shows capture efficiency (CE) vs time for a range of pore depths and capture radii.

FIG. 8 plots the capture efficiency from simulations as a function of two parameters that can be adjusted experimentally, pore depth and capture radius of the αHL. FIG. 8 shows capture efficiency (CE) vs time for a range of pore depths (0.5 and 1 µm) and capture radii (5, 10, 25 nm). Pore half-angle 10°, tip radius 100 nm. One can see that the increased pore volume when the pore depth is 1 µm gives systematically longer capture times when compared to the 0.5 µm case. Moreover, the capture time decreases as the capture radius, a, increases. These trends are precisely as predicted by equations 10 and 11. In all cases the time to obtain complete capture is on the time scale of milliseconds, such that the identity of each monomeric unit or NMP can be readily determined and released into the bulk, long before the next monomeric unit or NMP is released by the enzyme or exonuclease.

Theoretical Conclusions

Fast diffusion of the nucleotide means rapid mixing of the probability function. This means that in a very short time after the nucleotide is released at the bottom of the nanopore/nanowell electrode it has an almost equal probability to be found anywhere within the confined volume. This means it has a very high probability to encounter the region close to the αHL from which it will be captured, translocated, sequenced and read within a short time. The time-scales calculated can be characterized by the time constant of an exponential decay (π=Vol/2πaD.), and for achievable nanopore volumes, this means that the nucleotide is almost certainly sequenced within ~1 ms. This value being close to the most rapid operating frequency of an exonuclease indicates the plausibility of this method of nucleic acid sequencing. The reasons that sequencing works in this way is because the monomers or NMPs that the exonuclease enzyme is releasing are confined to a small volume, which insures that they are captured and read by the transmembrane channel. Non-limiting examples of the confined volumes of the nanopore/nanowell chamber that are enable the nanopore/nanowell electrode exonuclease sequencing concept include 0.01 femtoliters (fl), 0.1 fl, 1 fl, 5 fl, 10 fl, 50 fl, 100 fl, 500 fl, 750 fl, 1 picoliters (pl), 5 pl, 10 pl, 25 pl, 50 pl, 100 pl, 200 pl, 300 pl, 400 pl, 500 pl, 600 pl, 700 pl, 800 pl, 900 pl, 1 nanoliters (nl), 2 nl, 3 nl.

Listing of Certain Embodiments

Provided hereafter is a listing of certain non-limiting examples of embodiments of the technology.

A1. A device comprising:
a substrate comprising a chamber comprising a proximal opening, a distal opening, sidewalls and an interior volume;
a first seal over the proximal opening of the chamber and a second seal over the distal opening of the chamber; whereby the interior volume of the chamber is a confined volume;
a transmembrane channel in the first seal;
an enzyme attached to an interior surface of the chamber; and
a component configured to detect an interaction between a molecule and the transmembrane channel.

A2. The device of embodiment A1, wherein the enzyme can cleave one or more monomeric units from a polymer.

A2.1. The device of embodiment A2, wherein the enzyme has exonuclease activity.

A2.2. The device of embodiment A2, wherein the enzyme has endonuclease activity.

A2.3. The device of any one of embodiments A1 to A2.2, wherein the component comprises a first electrode external to a chamber and opposed to but not covering the proximal opening of the chamber and a second electrode external to a chamber, opposed to and not covering the distal opening of the chamber and not in contact with the second seal, a second electrode external to a chamber, opposed to and not covering the distal opening of the chamber and in contact with the second seal or a second electrode covering the distal opening of the chamber and the second seal comprises the second electrode.

A2.4. The device of embodiment A2.3, wherein the component comprises a controllable voltage source associated with a capacity for DC and/or AC current measurements.

A3. The device of any one of embodiments A1 to A2.4, wherein detecting an interaction between the molecule and the channel comprises measuring a change in conductance of the channel.

A4. The device of any one of embodiments A1 to A2.4, wherein detecting an interaction between the molecule and the channel comprises detecting a current signature, translocation time, and/or an associated current noise level modulation.

A5. The device of any one of embodiments A1 to A4, comprising a component configured to resolve and trigger high speed DC bias reversal.

A6. The device of any one of embodiments A1 to A5, wherein the first seal is a planar lipid bilayer, a triblock copolymer or a first membrane.

A7. The device of embodiment A1 to A6, wherein the transmembrane channel is a nanopore, an ion channel or a transmembrane protein.

A7.1. The device of embodiment A7, wherein the transmembrane channel is a biological nanopore, an ion channel or a transmembrane protein and the first seal is a planar lipid bilayer or a triblock copolymer.

A7.2. The device of embodiment A7, wherein the transmembrane channel is a nanopore, the nanopore is a solid state nanopore and the first seal is a first membrane.

A7.3. The device of embodiment A7.2, wherein the first membrane is Si, SiN, $Si_3N_4$, $SiO_2$, glass, quartz, aluminum, kapton, paralene, polyimide, diamond, or fused silica or combinations thereof.

A8. The device of any one of embodiments A1 to A7.1, wherein the transmembrane channel is alpha-hemolysin (αHL), aerolysin, *Mycobacterium smegmatis* porin A (MspA), *Escherichia coli* CsgG, or outer membrane protein F (OmpF).

A9. The device of any one of embodiments A1 to A8, wherein the molecule is a monomeric unit of a polymer and/or a polymer.

A9.1. The device of embodiments A9, wherein the molecule is a polymer and the transmembrane channel can translocate the polymer.

A9.2. The device of embodiment A9.1, wherein the polymer is a nucleic acid.

A9.3. The device of embodiment A9.2, wherein the nucleic acid is single stranded RNA or single stranded DNA.

A9.4. The device of embodiment A9.1, wherein the translocation is facilitated by electrophoresis and/or electroosmosis modulated by the component comprising a controllable voltage source associated with a capacity for DC and/or AC current measurements.

A9.5. The device of embodiment A9, wherein the molecule is a monomeric unit of a polymer.

A9.6. The device of embodiment A9.5, wherein the monomeric unit is a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide.

A9.7. The device of embodiment A9.5 or A9.6, wherein the transmembrane channel can translocate the monomeric unit of the polymer.

A9.8. The device of embodiment A9.7, wherein the translocation is facilitated by electrophoresis and/or electroosmosis modulated by the component comprising a controllable voltage source associated with a capacity for DC and/or AC current measurements.

A10. The device of any one of embodiments A1 to A9.8, wherein the transmembrane channel is a mutated, engineered, chemically modified, or is a mutant form.

A11. The device of embodiment A10, wherein the transmembrane channel is modified via site directed mutagenesis or chemical modification.

A11.1. The device of embodiment A10, wherein the transmembrane channel is modified with an adaptor molecule.

A12. The device of any one of embodiments A10 or A11.1, wherein the transmembrane channel includes a modification at the entrance of the transmembrane channel on the cis side and/or a modification at the exit of the transmembrane channel on the trans side.

A13. The device of embodiment A12, wherein the molecule is a monomeric unit of a polymer and/or a polymer and the modification of the channel lowers the energy barrier of entry into the channel of a polymer translocating into the confined volume and/or lowers the energy barrier of entry into the channel of a monomeric unit of the polymer translocating out of the confined volume.

A14. The device of embodiment A10 or A11, wherein the molecule is a monomeric unit of a polymer and the modification of the transmembrane channel increases the contrast between monomeric units as they translocate through the channel.

A15. The device of embodiment A14, wherein the modification is a reduction of negative charge within the channel, an increase in positive charge within the channel, a reduction in overall channel charge, a reduction in cross sectional width of a channel, an elongation of a sensing zone of the channel, the incorporation of electrostatic or van der Waal traps within the channel or the sensing zone, an increase in the nonpolar groups within the channel or combinations thereof.

A16. The device of any one of embodiments A1 to A15, wherein the second electrode is exterior to the chamber, opposed to and not covering the distal opening of the chamber and not in contact with the second seal or the second electrode is external to a chamber, opposed to and not covering the distal opening of the chamber and contacts the second seal.

A16.1. The device of embodiment A16, wherein the second seal comprises a porous material that conducts ions in solution and does not transport a polymer, a nucleic acid, single stranded RNA, single stranded DNA, a monomeric unit of a polymer, a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide.

A17. The device of embodiment A16.1, wherein the material is graphene, graphene oxide, boron nitride, carbon nanotubes, molybdenum disulfide, chemically modified glass frit, sol-gel, chemically modified sol-gel, or chemically modified anodic aluminum oxide.

A18. The device of embodiment A16, wherein the second seal is a second membrane that conducts ions in solution and does not transport a polymer, a nucleic acid, single stranded RNA, single stranded DNA, a monomeric unit of a polymer, a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide.

A19. The device of embodiment A18, wherein the membrane is a proton exchange polymer membrane, an anion exchange polymer membrane, a conductive ion exchange polymer membrane, an ion exchange redox polymer, an redox doped conducting polymer or an oil and water ion transfer membrane.

A20. The device of embodiment A16, wherein the second seal comprises nanopores, ion channels, porins or transmembrane nanopores in a lipid bilayer or triblock copolymer.

A21. The device of any one of embodiments A2.1 to A15, wherein the second seal comprises the second electrode.

A21.1. The device of embodiment A21, wherein the chamber is above the second electrode.

A22. The device of embodiment A21.1, wherein the second electrode is comprised of Au, Ag, Ag/AgCl, Pt, or combinations thereof.

A23. The device of any one of embodiments A1 to A20, wherein the first and second electrodes are comprised of Au, Ag, Ag/AgCl, Pt, or combinations thereof.

A24. The device of any one of embodiments A1 to A23, wherein there is a single enzyme molecule.

A25. The device of any one of embodiments A1 to A23, wherein there are two or more enzyme molecules.

A26. The device of embodiment A21, wherein the second seal is a second electrode.

A26.1. The device of any one of embodiments A1 to A26, wherein an enzyme is covalently attached, attached via a linker or attached with binding pairs to the inner surface of the chamber.

A26.2. The device of any one of embodiments A1 to A26.1, wherein the enzyme is attached to a side wall of the chamber.

A26.3. The device of embodiment A26.2, wherein the enzyme is attached to a metallic layer in the sidewall of the chamber.

A27. The device of any one of embodiments A1 to A26.1, wherein a second electrode covers the distal opening of the chamber, the second seal comprises the second electrode and an enzyme is attached to the electrode.

A28. The device of any one of embodiments A1 to A27, wherein the enzyme is attached to an inner surface of the chamber at a distance from the first seal of about 10 nanometers to about 10 micrometers.

A29. The device of any one of embodiments A1 to A28, wherein the substrate is Si, SiN, $Si_3N_4$, $SiO_2$, glass, quartz, aluminum, kapton, paralene, polyimide, diamond, or fused silica or combinations thereof.

A30. The device of any one of embodiments A1 to A29, wherein the substrate is modified to aid in the ability to wet the inside of the substrate, alter the electrical properties of the substrate, aid planar lipid bilayer formation and stability, limit or prevent non-specific adsorption, and/or alter or remove the charge associated with the walls of the substrate.

A31. The device of any one of embodiments A1 to A30 wherein the chamber is a nanowell.

A32. The device of any one of embodiments A1 to A31, wherein the depth of the chamber from proximal opening to distal opening is about 20 nanometers to about 10 micrometers.

A33. The device of any one of embodiments A1 to A32, wherein the width of the proximal opening of the chamber is about 20 nanometers to about 5 micrometers.

A34. The device of any one of embodiments A1 to A33, wherein the chamber is conical, cylindrical, cubical, trapezoidal, triangular, pyramidal or cuboidal.

A35. The device of any one of embodiments A1 to A34, wherein the confined volume of the chamber is about 1 zeptoliter to about 1 nanoliter.

A36. The device of any one of embodiments A1 to A35, wherein the confined volume of the chamber contains an aqueous solution of a buffered electrolyte or an ionic solution.

A37. The device of any one of embodiments A1 to A36, wherein the transmembrane channel is modified or coated to limit or prevent non-specific adsorption and/or control electroosmosis through the channel.

B1. A multiplex device comprising more than one of the devices of embodiments A1 to A37.

C1. A method for determining the sequence of a polymer, comprising:
  a) electrophoretically and/or electroosmotically driving a polymer from a bulk solution through a transmembrane channel into a confined volume of a chamber; whereby the polymer contacts an enzyme in the confined volume of the chamber, under conditions in which the enzyme cleaves monomeric units from the polymer;
  b) electrophoretically and/or electroosmotically driving monomeric units in the order which they are sequentially cleaved from the polymer by the enzyme out of the confined volume of the chamber through the transmembrane channel; and
  c) determining the identity of each of the monomeric units based on its current signature, translocation time, and/or associated current noise level modulation as the monomeric unit translocates through the transmembrane channel, thereby determining the sequence of the polymer.

C2. The method of embodiment C1, wherein the polymer is a single polymer molecule.

C3. The method of embodiment C2, wherein detection of a single translocation conductance spike confirms translocation of a single polymer molecule into the confined volume of the chamber.

C4. The method of any one of embodiments C1 to C3, wherein voltage bias is decreased after step a.

C5. The method of any one of embodiments C1 to C4, wherein step b is carried out after an enzyme capture probability time.

C6. The method of embodiment C5, wherein enzyme capture probability time is about 1 microsecond to about 10 minutes.

C7. The method of any one of embodiments C1 to C6, wherein step b comprises reversing drive bias polarity.

C8. The method of any one of embodiments C1 to C7, wherein a monomeric unit, after being cleaved or released from the polymer, encounters and translocates through the transmembrane channel in a period of time less than or equal to the maximum operating frequency of the enzyme.

C9. The method of any one of embodiments C1 to C8, wherein a monomeric unit encounters and translocates through the transmembrane channel within about 10 microseconds to about 5 seconds.

C10. The method of any one of embodiments C1 to C9, wherein the polymer is single stranded RNA or single stranded DNA.

C11. The method of embodiment C10, wherein the sequence of the entire polymer is determined.

C12. The method of embodiment C10, wherein the sequence of a portion of the polymer is determined.

C13. The method of any one of embodiments C1 to C12, wherein the monomeric unit is a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide, C14. The method of any one of embodiments C1 to C13, wherein the viscosity of the aqueous solution of a buffered electrolyte or of the ionic solution is increased or decreased to a level that increases capture efficiency and/or measurable resolution of the polymer or monomeric unit by the transmembrane channel.

C15. The method of any one of embodiments C1 to C14, wherein the transmembrane channel is a nanopore, an ion channel or a transmembrane protein.

C16. The method of embodiment C15, wherein the transmembrane channel is a nanopore and the nanopore is a solid state nanopore.

C17. The method of embodiment C15, wherein the transmembrane channel is a nanopore and the nanopore is a biological nanopore.

C18. The method of any one of embodiments C1 to C17 comprising providing a device of any one of embodiments A1 to A37.

C19. The method of embodiment C18, comprising:
  providing the device with a bulk solution outside the chamber; and
  providing a polymer to the bulk solution.

C.20. The method of any one of embodiments C1 to C19, wherein the enzyme has exonuclease activity.

C.21. The method of any one of embodiments C1 to C19, wherein the enzyme has endonuclease activity.

D1. A method for determining the sequence of a polymer or a portion thereof, comprising:
  a) electrophoretically and/or electroosmotically driving a polymer from a bulk solution, through a transmembrane channel into a confined volume of a chamber; whereby the polymer contacts an enzyme in the confined volume of the chamber, under conditions in which the enzyme cleaves monomeric units from the polymer;

b) electrophoretically and/or electroosmotically driving a first monomeric unit cleaved from the polymer out of the confined volume of the chamber through the transmembrane channel;

c) upon detection of a translocation of the first monomeric unit through the transmembrane channel, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel into the confined volume of the chamber;

d) upon detection of a translocation of the first monomeric unit through the transmembrane channel, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel out of the confined volume of the chamber;

e) repeating steps c and d multiple times;

f) determining the identity of the first monomeric unit based on its current signature, translocation time, and/or associated current noise level modulation as the monomeric unit translocates through the transmembrane channel multiple times;

g) electrophoretically and/or electroosmotically driving a next monomeric unit sequentially cleaved from the polymer by the enzyme out of confined volume of the chamber through the transmembrane channel;

h) upon detection of a translocation of the next monomeric unit through the transmembrane channel, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel into the confined volume of the chamber;

i) upon the detection of a translocation of the next monomeric unit through the transmembrane channel, triggering a reversal of DC drive bias used to electrophoretically and/or electroosmotically drive the next monomeric units through the transmembrane channel, whereby the next monomeric unit is electrophoretically and/or electroosmotically driven back through the transmembrane channel out of the confined volume of the chamber;

j) repeating steps h and i multiple times;

k) determining the identity of the next monomeric unit based on its current signature, translocation time, and/or associated current noise level modulation as the next monomeric unit translocates through the transmembrane channel multiple times; and l) repeating steps g to k until the identity of all monomeric units of the polymer or a portion of the monomeric units of the polymer have been identified, thereby determining the sequence of the polymer or a portion thereof.

D2. The method of D1, wherein between steps f and g and k and l, the drive bias is reset.

D3. The method of embodiment D1 or D2, wherein the polymer is a single polymer molecule.

D4. The method of embodiment D3, wherein detection of a single translocation conductance spike confirms translocation of a single polymer molecule into the confined volume of the chamber.

D5. The method of any one of embodiments D1 to D4, wherein voltage bias is decreased after step a.

D6. The method of any one of embodiments D1 to D5, wherein step b is carried out after an enzyme capture probability time.

D7. The method of embodiment D6, wherein enzyme capture probability time is about 1 microsecond to about 10 minutes.

D8. The method of any one of embodiments D1 to D7, wherein step b comprises reversing drive bias polarity.

D9. The method of any one of embodiments D1 to D8, wherein a monomeric unit, after being cleaved or released from the polymer, encounters and translocates through the transmembrane channel in a period of time less than or equal to the maximum operating frequency of the enzyme.

D10. The method of any one of embodiments D1 to D9, wherein a monomeric unit encounters and translocates through the transmembrane channel within about 10 microseconds to about 5 seconds.

D11. The method of any one of embodiments D1 to D11, wherein the polymer is single stranded RNA or single stranded DNA.

D12. The method of embodiment D11, wherein the sequence of the entire polymer is determined.

D13. The method of embodiment D11, wherein the sequence of a portion of the polymer is determined.

D14. The method of any one of embodiments D1 to D13, wherein the monomeric unit is a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide, D15. The method of any one of embodiments D1 to D14, wherein the viscosity of the aqueous solution of a buffered electrolyte or of the ionic solution is increased or decreased to a level that increases capture efficiency and/or measurable resolution of the polymer or monomeric unit by the transmembrane channel.

D16. The method of any one of embodiments D1 to D15, wherein the transmembrane channel is a nanopore, an ion channel or a transmembrane protein.

D17. The method of embodiment D16, wherein the transmembrane channel is a nanopore and the nanopore is a solid state nanopore.

D18. The method of embodiment D16, wherein the transmembrane channel is a nanopore and the nanopore is a biological nanopore.

D19. The method of any one of embodiments D1 to D18, comprising
providing a device of any one of embodiments A1 to A37.

D20. The method of embodiment D19, comprising:
providing the device with a bulk solution outside the chamber; and
providing a polymer to the bulk solution.

D21. The method of any one of embodiments D1 to D20 wherein the enzyme has exonuclease activity.

D22. The method of any one of embodiments D1 to D20, wherein the enzyme has endonuclease activity.

E1. A method for determining the sequence of a polymer or a portion thereof, comprising:
a) electrophoretically and/or electroosmotically driving the polymer from the bulk solution, through the transmembrane channel into the confined volume of the chamber; whereby the polymer contacts an enzyme in the confined volume of the chamber, under conditions in which the enzyme cleaves monomeric units from the polymer;

b) electrophoretically and/or electroosmotically driving a first monomeric unit cleaved from the polymer by the enzyme out of the confined volume of the chamber through the transmembrane channel;
c) upon detection of a translocation of the first monomeric unit through the transmembrane channel triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel into the confined volume of the chamber;
d) after a period of about 5 microseconds to about 500 microseconds, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel out of the confined volume of the chamber;
e) after a period of about 5 microseconds to about 500 microseconds triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel into the confined volume of the chamber;
f) after a period of about 5 microseconds to about 500 microseconds, triggering a reversal of DC drive bias used to electrophoretically and/or electroosmotically drive the first monomeric unit through the transmembrane channel, whereby the first monomeric unit is electrophoretically and/or electroosmotically driven back through the transmembrane channel out of the confined volume of the chamber;
g) repeating steps e and f multiple times;
h) determining the identity of the first monomeric unit based on its current signature, translocation time, and/or associated current noise level modulation as the monomeric unit translocates through the transmembrane channel multiple times;
i) electrophoretically and/or electroosmotically driving a next monomeric unit sequentially cleaved from the polymer by the enzyme out of the confined volume of the chamber through the transmembrane channel;
j) upon detection of a translocation of the next monomeric unit through the transmembrane channel, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel into the confined volume of the chamber;
k) after a period of about 5 microseconds to about 500 microseconds, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel out the confined volume of the chamber;
l) after a period of about 5 microseconds to about 500 microseconds, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel into the confined volume of the chamber;
m) after a period of about 5 microseconds to about 500 microseconds, triggering a reversal of DC drive bias used to electrophoretically and/or electroosmotically drive the next monomeric unit through the transmembrane channel, whereby the next monomeric unit is electrophoretically and/or electroosmotically driven back through the transmembrane channel out the confined volume of the chamber;
n) repeating steps I and m multiple times;
o) determining the identity of the next monomeric unit based on its current signature, translocation time, and/or associated current noise level modulation as the next monomeric unit translocates through the transmembrane channel multiple times; and
p) repeating steps i to o until the identity of all monomeric units of the polymer or a portion of the monomeric units of the polymer have been identified, thereby determining the sequence of the polymer or a portion thereof.

E2. The method of E1, wherein between steps h and i and o and p, the drive bias is reset.

E3. The method of embodiment E1 or E2, wherein the polymer is a single polymer molecule.

E4. The method of embodiment E3, wherein detection of a single translocation conductance spike confirms translocation of a single polymer molecule.

E5. The method of any one of embodiments E1 to E4, wherein voltage bias is decreased after step a.

E6. The method of any one of embodiments E1 to E5, wherein step b is carried out after an enzyme capture probability time.

E7. The method of embodiment E6, wherein enzyme capture probability time is about 1 microsecond to about 10 minutes.

E8. The method of any one of embodiments E1 to E7, wherein step b comprises reversing drive bias polarity.

E9. The method of any one of embodiments E1 to E8, wherein a monomeric unit, after being cleaved or released from the polymer, encounters and translocates through the transmembrane channel in a period of time less than or equal to the maximum operating frequency of the enzyme.

E10. The method of any one of embodiments E1 to E9, wherein a monomeric unit initially encounters and translocates through the transmembrane channel within about 10 microseconds to about 5 seconds.

E11. The method of any one of embodiments E1 to E1 11, wherein the polymer is single stranded RNA or single stranded DNA.

E12. The method of embodiment E11, wherein the sequence of the entire polymer is determined.

E13. The method of embodiment E11, wherein the sequence of a portion of the polymer is determined.

E14. The method of any one of embodiments E1 to E13, wherein the monomeric unit is a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide, E15. The method of any one of embodiments E1 to E14, wherein the viscosity of the aqueous solution of a buffered electrolyte or of the ionic solution is increased or decreased to a level that increases capture efficiency and/or measurable resolution of the polymer or monomeric unit by the transmembrane channel.

E16. The method of any one of embodiments E1 to E15, wherein the transmembrane channel is a nanopore, an ion channel or a transmembrane protein.

E17. The method of embodiment E16, wherein the transmembrane channel is a nanopore and the nanopore is a solid state nanopore.

E18. The method of embodiment E16, wherein the transmembrane channel is a nanopore and the nanopore is a biological nanopore.

E19. The method of any one of embodiments E1 to E18, comprising
providing a device of any one of embodiments A1 to A37.

E20. The method of embodiment E19, comprising:
providing the device with a bulk solution outside the chamber; and
providing a polymer to the bulk solution.

E21. The method of any one of embodiments E1 to E20 wherein the enzyme has exonuclease activity.

E22. The method of any one of embodiments E1 to E20, wherein the enzyme has endonuclease activity.

F1. A method for determining the identity of a molecule, comprising:
 a) electrophoretically and/or electroosmotically driving a molecule through a a transmembrane channel;
 b) upon the detection of a translocation of the molecule, triggering a reversal of the DC drive bias used to electrophoretically and/or electroosmotically drive the molecule through the transmembrane channel, whereby the molecule is driven back through the transmembrane channel;
 c) upon the detection of a translocation event, triggering a reversal of DC drive bias used to drive the molecule through the transmembrane channel, whereby the molecule is electrophoretically and/or electroosmotically driven back through the transmembrane channel;
 d) repeating b and c multiple times; and
 e) determining the identity of the molecule based on its current signature, translocation time, and/or associated current noise level modulation as it translocates through the transmembrane channel multiple times.

F2. The method of embodiment F1, wherein the molecule is an organic molecule, an inorganic molecule, an amino acid, a modified amino acid, a protein, a modified protein, a protein fragment, a modified protein fragment a peptide, a modified peptide, a polypeptide, a modified polypeptide, an antibody, an antigen, an antigen bound antibody, a cell, an extracellular vesicle, a polymer, a nucleotide monophosphate, a modified nucleotide monophosphate, a nucleoside monophosphate, a modified nucleoside monophosphate, a ribonucleic acid, a deoxyribonucleic acid, a ribonucleotide, a deoxyribonucleotide, a modified ribonucleotide or a modified deoxyribonucleotide.

F3. The method of embodiment F1 or F2, wherein the transmembrane channel is a nanopore, an ion channel or a transmembrane protein.

F4. The method of embodiment F3, wherein the transmembrane channel is a nanopore and the nanopore is a solid state nanopore.

F5. The method of embodiment F3, wherein the transmembrane channel is a nanopore and the nanopore is a biological nanopore.

G1. A method for determining the identity of a molecule, comprising:
 a) electrophoretically and/or electroosmotically driving a molecule through a transmembrane channel;
 b) upon the detection of a molecule translocation event, triggering a reversal of DC drive bias used to drive the molecule through the transmembrane channel, whereby the molecule is electrophoretically and/or electroosmotically driven back through the transmembrane channel;
 c) after a period of about 5 microseconds to about 500 microseconds, triggering a reversal of DC drive bias, whereby the molecule is electrophoretically and/or electroosmotically driven back through the transmembrane channel;
 d) after a period of about 5 microseconds to about 500 microseconds triggering a reversal of DC drive bias, whereby the molecule is electrophoretically and/or electroosmotically driven back through the transmembrane channel;
 e) repeating c and d multiple times; and
 f) determining the identity of the molecule based on its current signature, translocation time, and/or associated current noise level modulation as it translocates through the transmembrane channel multiple times.

G2. The method of embodiment G1, wherein the molecule is an organic molecule, an inorganic molecule, an amino acid, a modified amino acid, a protein, a modified protein, a protein fragment, a modified protein fragment a peptide, a modified peptide, a polypeptide, a modified polypeptide, an antibody, an antigen, an antigen bound antibody, a cell, an extracellular vesicle, a polymer, a nucleotide monophosphate, a modified nucleotide monophosphate, a nucleoside monophosphate, a modified nucleoside monophosphate, a ribonucleic acid, a deoxyribonucleic acid, a ribonucleotide, a deoxyribonucleotide, a modified ribonucleotide or a modified deoxyribonucleotide.

G3. The method of embodiment G1 or G2, wherein the transmembrane channel is a nanopore, an ion channel or a transmembrane protein.

G4. The method of embodiment G3, wherein the transmembrane channel is a nanopore and the nanopore is a solid state nanopore.

G5. The method of embodiment D3, wherein the transmembrane channel is a nanopore and the nanopore is a biological nanopore.

H1. A device, comprising:
 a substrate comprising a chamber that comprises a proximal opening, a distal opening, an interior volume and an electrode enclosing the distal opening of the chamber;
 an enzyme having exonuclease activity attached to the electrode, wherein the enzyme optionally is attached by a covalent attachment to the electrode;
 a planar lipid bilayer suspended over the proximal opening of the chamber and enclosing the interior volume;
 a transmembrane channel in the planar lipid bilayer; and
 a component configured to detect an interaction between a molecule and the transmembrane channel.

H2. The device of embodiment H1, wherein the electrode is comprised of Au.

H3. The device of embodiment H1 or H2, wherein the enzyme is attached to the electrode via a linker.

H4. The device of embodiment H1, wherein the molecule is a monomer and/or polymer.

H5. The device of any one of embodiments H1 to H4, wherein the transmembrane channel is a wild type nanopore, ion channel or transmembrane protein.

H6. The device of embodiment H5, wherein the transmembrane channel is alpha-hemolysin (αHL), aerolysin, *Mycobacterium smegmatis* porin A (MspA), *Escherichia coli* CsgG, or outer membrane protein F (OmpF).

H7. The device of any one of embodiments H1 to H6, wherein the transmembrane channel is a mutated, engineered, chemically modified, or mutant form.

H8. The device of embodiment H7, wherein the transmembrane channel is alpha-hemolysin (αHL), aerolysin, *Mycobacterium smegmatis* porin A (MspA), *Escherichia coli* CsgG, or outer membrane protein F (OmpF).

H9. The device of embodiment H7 or H8, wherein the transmembrane channel is modified via site directed mutagenesis or chemical modification.

H10. The device of any one of embodiments 7 to 9, wherein the transmembrane channel includes a modification that lowers the energy barrier of entry of the molecule, thus increasing the capture rate or efficiency of the monomer by the transmembrane channel.

H11. The device of any one of embodiments H1 to H10, wherein the depth of the chamber from proximal opening to distal opening is less than 5 μm, less than 2 μm, less than 1 μm, less than 800 nm, less than 500 nm, less than 400 nm, less than 300 nm, less than 200 nm, or less than 100 nm.

H12. The device of any one of embodiments H1 to H11, wherein the width of the proximal opening of the chamber is less than 10 μm, less than 5 μm, less than 2 μm, less than 1 μm, less than 800 nm, less than 500 nm, less than 400 nm, less than 300 nm, less than 200 nm, less than 100 nm, or less than 50 nm.

H13. The device of any one of embodiments H1 to H12, wherein the volume of the chamber is less than 0.01 fl, less than 0.1 fl, less than 1 fl, less than 5 fl, less than 10 fl, less than 50 fl, less than 100 fl, less than 500 fl, less than 750 fl, less than 1 pl, less than 5 pl, less than 10 pl, less than 25 pl, less than 50 pl, less than 100 pl, less than 200 pl, less than 300 pl, less than 400 pl, less than 500 pl, less than 600 pl, less than 700 pl, less than 800 pl, less than 900 pl, less than 1 nl, less than 2 nl, or less than 3 nl.

I1. A method for determining the sequence of a polymer, comprising:
(A) providing a device of any one of embodiments H1 to H13 with a bulk solution outside the chamber comprising a polymer;
(B) electrophoretically driving the polymer from the bulk solution, through the transmembrane channel into the interior volume of the chamber under conditions in which the enzyme can cleave monomers from the polymer;
(C) electrophoretically driving the monomers out of the enclosed chamber volume through the transmembrane channel in sequential order;
(D) determining the identity of the monomers based on its current signature as it translocates through the transmembrane channel; and
(E) repeating C and D until the sequence of the polymer is determined.

I2. The method of embodiment I1, wherein the polymer is single stranded RNA or single stranded DNA.

I3. The method of embodiment I1 or I2, wherein the sequence of the polymer is ascertained completely.

I4. The method of embodiment I1 or I2, wherein the sequence of the polymer is partially ascertained.

I5. The method of any one of embodiments I1 to I4, wherein the monomer is a molecule, analyte, nucleotide monophosphate, nucleoside monophosphate, ribonucleic acid, deoxyribonucleic acid, ribonucleotide, deoxyribonucleotide, or monomeric unit of a polymer.

I6. The method of any one of embodiments I1 to I5, wherein the viscosity of the solution is increased or decreased to a level that increases the capture efficiency and/or measurable resolution of the polymer or monomer by the transmembrane channel.

J1. A method for determining the sequencing of a polymer, comprising:
(A) providing a device of any one of embodiments H1 to H13 with a bulk solution outside the chamber comprising a polymer;
(B) electrophoretically driving the polymer from the bulk solution, through the transmembrane channel into the interior volume of the chamber under conditions in which the enzyme can cleave monomers from the polymer;
(C) electrophoretically driving the monomers out of the enclosed chamber volume through the transmembrane channel in sequential order;
(D) upon the detection of the monomer translocation event, triggering a reversal of the DC drive bias used to electrophoretically drive the monomer through the transmembrane channel, such that the monomer is electrophoretically driven back through the transmembrane channel back into the chamber;
(E) upon the detection of the translocation event, triggering a reversal of the DC drive bias used to electrophoretically drive the monomer through the transmembrane channel, such that the monomer is electrophoretically driven back through the transmembrane channel back out of the chamber;
(F) repeating D and E a set number of times;
(G) determining the identity of the monomers based on its current signature as it translocates through the transmembrane channel multiple times; and
(H) repeating D, E, F and G until the sequence of the polymer is determined.

J2. The method of embodiment J1, wherein the polymer is single stranded RNA or single stranded DNA.

J3. The method of embodiment J1 or J2, wherein the sequence of the polymer is ascertained completely.

J4. The method of embodiment J1 or J2, wherein the sequence of the polymer is partially ascertained.

J5. The method of any one of embodiments J1 to J4, wherein the monomer is a molecule, analyte, nucleotide monophosphate, nucleoside monophosphate, ribonucleic acid, deoxyribonucleic acid, ribonucleotide, deoxyribonucleotide or monomeric unit of a polymer.

J6. The method of any one of embodiments J1 to J5, wherein the viscosity of the solution is increased or decreased to a level that increases the capture efficiency and/or measurable resolution of the polymer or monomer by the transmembrane channel.

K1. A method for determining the sequencing of a polymer, comprising:
(A) providing a device of any one of embodiments H1 to H13 with a bulk solution outside the chamber comprising a polymer;
(B) electrophoretically driving the polymer from the bulk solution, through the transmembrane channel into the interior volume of the chamber under conditions in which the enzyme can cleave monomers from the polymer;
(C) electrophoretically driving the monomers out of the enclosed chamber volume through the transmembrane channel in sequential order;
(D) upon the detection of the monomer translocation event, triggering a reversal of the DC drive bias used to electrophoretically drive the monomer through the transmembrane channel, such that the monomer is electrophoretically driven back through the transmembrane channel back into the chamber;
(E) after a set amount of time, triggering a reversal of the DC drive bias such that the monomer is electrophoretically driven back through the transmembrane channel back out of the chamber;
(F) after a set amount of time, triggering a reversal of the DC drive bias such that the monomer is electrophoretically driven back through the transmembrane channel back into the chamber;
(G) repeating E and F a set number of times;
(I) determining the identity of the monomers based on its current signature as it translocates through the transmembrane channel multiple times; and
(J) repeating E, F, G and I until the sequence of the polymer is determined.

K2. The method of embodiment K1, wherein the polymer is single stranded RNA or single stranded DNA.

K3. The method of embodiment K1 or K2, wherein the sequence of the polymer is ascertained completely.

K4. The method of embodiment K1 or K2, wherein the sequence of the polymer is partially ascertained.

K5. The method of any one of embodiments K1 to K4, wherein the monomer is a molecule, analyte, nucleotide monophosphate, nucleoside monophosphate, ribonucleic acid, deoxyribonucleic acid, ribonucleotide, deoxyribonucleotide, or monomeric unit of a polymer.

K6. The method of any one of embodiments K1 to K5, wherein the viscosity of the solution is increased or decreased to a level that increases the capture efficiency and/or measurable resolution of the polymer or monomer by the transmembrane channel.

L1. A method for determining the identity of a molecule, comprising:
(A) electrophoretically driving the molecule through a transmembrane channel;
(B) upon the detection of the molecule translocation event, triggering a reversal of the DC drive bias used to electrophoretically drive the molecule through the transmembrane channel, such that the molecule is electrophoretically driven back through the transmembrane channel;
(C) upon the detection of the translocation event, triggering a reversal of the DC drive bias used to electrophoretically drive the molecule through the transmembrane channel, such that the molecule is electrophoretically driven back through the transmembrane channel;
(D) repeating B and C a set number of times; and
(E) determining the identity of the molecule based on its current signature as it translocates through the transmembrane channel multiple times;

L2. The method of embodiment L1, wherein the molecule is an analyte, organic molecule, inorganic molecule, amino acid, peptide, polypeptide, nucleotide monophosphate, nucleoside monophosphate, ribonucleic acid, deoxyribonucleic acid, ribonucleotide, deoxyribonucleotide, monomeric unit of a polymer, or unit of a polymer.

M1. A method for determining the identity of a molecule, comprising:
(A) electrophoretically driving the molecule out through a transmembrane channel;
(B) upon the detection of the molecule translocation event, triggering a reversal of the DC drive bias used to electrophoretically drive the molecule through the transmembrane channel, such that the molecule is electrophoretically driven back through the transmembrane channel;
(C) after a set amount of time, triggering a reversal of the DC drive bias such that the molecule is electrophoretically driven back through the transmembrane channel;
(D) after a set amount of time, triggering a reversal of the DC drive bias such that the molecule is electrophoretically driven back through the transmembrane channel;
(E) repeating C and D a set number of times; and
(F) determining the identity of the molecule based on its current signature as it translocates through the transmembrane channel multiple times;

M2. The method of embodiment M1, wherein the molecule is an analyte, organic molecule, inorganic molecule, amino acid, peptide, polypeptide, nucleotide monophosphate, nucleoside monophosphate, ribonucleic acid, deoxyribonucleic acid, ribonucleotide, deoxyribonucleotide, monomeric unit of a polymer, or unit of a polymer.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A nanopore/nanowell electrode device comprising:
   a substrate comprising a chamber comprising a proximal opening, a distal opening, sidewalls and an interior volume;
   a first seal over the proximal opening of the chamber and a second seal over the distal opening of the chamber; whereby the interior volume of the chamber is a confined volume less than 10 femtoliters;
   a transmembrane channel in the first seal oriented with a channel entrance exposed to a solution outside the nanopore electrode device (cis) and a channel exit exposed to a solution inside the nanopore electrode device (trans);
   an enzyme attached to an interior surface of the chamber at a distance from the first seal greater than 100 nm to about 2000 nm; and
   a component configured to detect an interaction between a molecule and the transmembrane channel.

2. The device of claim 1, wherein the enzyme can cleave one or more monomeric units from a polymer.

3. The device of claim 2, wherein the polymer is single stranded RNA or single stranded DNA.

4. The device of claim 2, wherein the monomeric unit is a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide.

5. The device of claim 1, wherein the enzyme is attached to an interior surface of the chamber at a distance from the first seal of about 500 nm to about 1000 nm.

6. The device of claim 1, wherein the interior volume of the chamber is a confined volume of about 1 attoliter to about 1 femtoliter.

7. The device of claim 1, wherein the component configured to detect an interaction between the molecule and the channel is configured to comprises detecting a current signature, translocation time, and/or an associated current noise level modulation.

8. The device of claim 1, wherein the transmembrane channel is a biological nanopore, an ion channel or a transmembrane protein.

9. The device of claim 8, wherein the first seal is a planar lipid bilayer or a triblock copolymer.

10. The device of claim 8, wherein the transmembrane channel is a transmembrane protein and the transmembrane protein is alpha-hemolysin (αHL), aerolysin, mycobacterium smegmatis porin A (MspA), Escherichia coli CsgG, or outer membrane protein F (OmpF).

11. The device of claim 1, wherein the transmembrane channel is a solid state nanopore and the first seal is a first membrane.

12. The device of claim 1, wherein the transmembrane channel is a mutated, engineered, chemically modified, or is a mutant form comprising a modification of the transmembrane channel.

13. The device of claim 1, wherein the transmembrane channel contains a molecular adaptor configured to narrow the diameter of the transmembrane channel.

14. The device of claim 1, wherein the second seal is a second membrane.

15. The device of claim 14, wherein the second membrane conducts ions in solution and does not transport a polymer, a nucleic acid, single stranded RNA, single stranded DNA, a monomeric unit of a polymer, a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide.

16. The device of claim 1, wherein the enzyme is attached to the second seal.

17. The device of claim 1, wherein the enzyme is attached to a metallic layer on the interior surface of the chamber.

18. The device of claim 1, wherein the enzyme is attached to a side wall of the chamber.

19. The device of claim 1, wherein the length from the proximal opening to the distal opening of the chamber is less than 5 micrometers.

20. The device of claim 1, wherein the second seal comprises a porous material that conducts ions in solution and does not transport a polymer, a nucleic acid, single stranded RNA, single stranded DNA, a monomeric unit of a polymer, a nucleotide monophosphate, a modified nucleotide monophosphate, a nucleoside monophosphate, a modified nucleoside monophosphate, a ribonucleotide, a deoxyribonucleotide, a modified ribonucleotide or a modified deoxyribonucleotide.

21. The device of claim 20, wherein the second seal porous material is graphene, graphene oxide, boron nitride, carbon nanotubes, molybdenum disulfide, chemically modified glass frit, sol-gel, chemically modified sol-gel, or chemically modified anodic aluminum oxide.

22. A multiplex device comprising a plurality of devices of claim 1.

23. A method for determining the sequence of a polymer, comprising
   a) providing the nanopore/nanowell device of claim 1;
   b) electrophoretically and/or electroosmotically driving a polymer from a bulk solution through the transmembrane channel into the interior volume of the chamber, whereby the polymer contacts the enzyme attached to the interior surface of the chamber, under conditions in which the enzyme cleaves monomeric units from the polymer;
   c) electrophoretically and/or electroosmotically driving monomeric units in the order which they are sequentially cleaved from the polymer by the enzyme out of the interior volume of the chamber through the transmembrane channel; wherein a monomeric unit encounters and is translocated through the transmembrane channel in less than 300 milliseconds; and
   d) determining the identity of each of the monomeric units based on its current signature, translocation time, and/or associated current noise level modulation as the monomeric unit translocates through the transmembrane channel, thereby determining the sequence of the polymer.

* * * * *